United States Patent
Nasr et al.

(10) Patent No.: US 11,938,022 B2
(45) Date of Patent: Mar. 26, 2024

(54) TRANSCATHETER VALVE PROSTHESIS AND METHOD FOR IMPLANTING THE SAME

(71) Applicant: HIGHLIFE SAS, Paris (FR)

(72) Inventors: Malek Nasr, Paris (FR); Georg Börtlein, Paris (FR)

(73) Assignee: HIGHLIFE SAS, Paris (FR)

( * ) Notice: Subject to any disclaimer, the term of this patent is extended or adjusted under 35 U.S.C. 154(b) by 186 days.

(21) Appl. No.: 17/329,724

(22) Filed: May 25, 2021

(65) Prior Publication Data

US 2021/0401572 A1 Dec. 30, 2021

Related U.S. Application Data

(60) Provisional application No. 63/044,534, filed on Jun. 26, 2020.

(51) Int. Cl.
*A61F 2/24* (2006.01)

(52) U.S. Cl.
CPC .... *A61F 2/2418* (2013.01); *A61F 2220/0016* (2013.01); *A61F 2220/0083* (2013.01)

(58) Field of Classification Search
CPC ............ A61F 2/2418; A61F 2220/0016; A61F 2220/0083; A61F 2250/0039; A61F 2/2436; A61F 2/24; A61F 2/2409; A61F 2/2427
See application file for complete search history.

(56) References Cited

U.S. PATENT DOCUMENTS

| | | | |
|---|---|---|---|
| 6,120,534 A | 9/2000 | Ruiz | |
| 7,806,927 B2 | 10/2010 | Styrc | |
| 8,236,049 B2 | 8/2012 | Rowe et al. | |
| 8,323,335 B2 | 12/2012 | Rowe et al. | |
| 8,449,605 B2 | 5/2013 | Lichtenstein et al. | |
| 8,597,348 B2 | 12/2013 | Rowe et al. | |
| 8,623,079 B2 | 1/2014 | Savage et al. | |

(Continued)

FOREIGN PATENT DOCUMENTS

| | | |
|---|---|---|
| DE | 697 30 840 T2 | 9/2005 |
| DE | 102005052628 A1 | 5/2007 |

(Continued)

OTHER PUBLICATIONS

Boudjemline et al. "Steps Toward Percutaneous Aortic Valve Replacement," Circulation, vol. 105, Feb. 2002, pp. 775-778.

(Continued)

*Primary Examiner* — Christopher D. Prone
(74) *Attorney, Agent, or Firm* — Oliff PLC

(57) ABSTRACT

A transcatheter valve prosthesis and a method for implanting the prosthesis in a heart are disclosed. The prosthesis includes a tubular body a coupled to a prosthetic valve. A fabric may be disposed on an outer surface of the tubular body. The method includes partially deploying the tubular body from a catheter to at position distal of a distal edge of a native valve leaflet, and moving the catheter such that the deployed outflow end portion of the tubular body engages the distal edge of the native valve leaflet and lifts the native valve leaflet in the proximal direction towards an atrial chamber of the heart. Then, the tubular body can be fully deployed such that the native valve leaflet is captured between the outflow end portion and the inflow end portion.

20 Claims, 11 Drawing Sheets

(56) References Cited

U.S. PATENT DOCUMENTS

| | | |
|---|---|---|
| 8,956,404 B2 | 2/2015 | Bortlein et al. |
| 9,358,108 B2 | 6/2016 | Bortlein et al. |
| 9,375,312 B2 | 6/2016 | Weber |
| 9,387,075 B2 | 7/2016 | Bortlein et al. |
| 9,662,206 B2 | 5/2017 | Bortlein et al. |
| 9,687,343 B2 | 6/2017 | Bortlein et al. |
| 9,763,779 B2 | 9/2017 | Bortlein et al. |
| 9,889,003 B2 | 2/2018 | Bortlein et al. |
| 9,931,206 B2 | 4/2018 | Weber |
| 10,064,719 B2* | 9/2018 | Börtlein ............... A61F 2/2418 |
| 10,080,651 B2 | 9/2018 | Bortlein et al. |
| 10,828,157 B2 | 11/2020 | Bortlein et al. |
| 2001/0039450 A1* | 11/2001 | Pavcnik ................ A61F 2/01 623/1.36 |
| 2002/0055774 A1 | 5/2002 | Liddicoat |
| 2002/0099438 A1 | 7/2002 | Furst |
| 2002/0193871 A1 | 12/2002 | Beyersdorf et al. |
| 2003/0070683 A1 | 4/2003 | Deem et al. |
| 2003/0125798 A1* | 7/2003 | Martin .................. A61F 2/82 623/1.13 |
| 2004/0015232 A1 | 1/2004 | Shu et al. |
| 2004/0044406 A1 | 3/2004 | Woolfson et al. |
| 2004/0186565 A1 | 9/2004 | Schreck |
| 2004/0210304 A1* | 10/2004 | Seguin .................. A61F 2/2409 623/2.11 |
| 2004/0243227 A1 | 12/2004 | Starksen et al. |
| 2005/0049681 A1* | 3/2005 | Greenhalgh ..... A61B 17/12022 623/1.15 |
| 2005/0055082 A1 | 3/2005 | Ben Muvhar et al. |
| 2005/0060029 A1* | 3/2005 | Le ....................... A61F 2/2418 623/2.11 |
| 2005/0113910 A1* | 5/2005 | Paniagua .............. A61F 2/2412 623/2.14 |
| 2005/0137686 A1 | 6/2005 | Salahieh et al. |
| 2005/0182486 A1 | 8/2005 | Gabbay |
| 2006/0058872 A1 | 3/2006 | Salahieh et al. |
| 2007/0027534 A1* | 2/2007 | Bergheim ............. A61F 2/2427 623/2.11 |
| 2007/0129795 A1 | 6/2007 | Hill et al. |
| 2007/0142906 A1 | 6/2007 | Figulla et al. |
| 2007/0142907 A1 | 6/2007 | Moaddeb et al. |
| 2007/0213813 A1 | 9/2007 | Von Segesser et al. |
| 2008/0071361 A1 | 3/2008 | Tuval et al. |
| 2008/0071369 A1 | 3/2008 | Tuval et al. |
| 2008/0077234 A1 | 3/2008 | Styrc |
| 2008/0077236 A1 | 3/2008 | Letac et al. |
| 2009/0319037 A1 | 12/2009 | Rowe et al. |
| 2010/0094411 A1 | 4/2010 | Tuval et al. |
| 2010/0145438 A1 | 6/2010 | Barone |
| 2010/0256751 A1 | 10/2010 | Rowe et al. |
| 2010/0298931 A1 | 11/2010 | Quadri et al. |
| 2010/0312333 A1 | 12/2010 | Navia et al. |
| 2011/0137397 A1 | 6/2011 | Chau et al. |
| 2011/0218620 A1 | 9/2011 | Meiri et al. |
| 2011/0224785 A1 | 9/2011 | Hacohen |
| 2011/0238168 A1 | 9/2011 | Pellegrini et al. |
| 2011/0264196 A1 | 10/2011 | Savage et al. |
| 2011/0313515 A1 | 12/2011 | Quadri et al. |
| 2011/0319988 A1 | 12/2011 | Schankereli et al. |
| 2012/0022640 A1 | 1/2012 | Gross et al. |
| 2012/0035722 A1 | 2/2012 | Tuval |
| 2012/0053682 A1 | 3/2012 | Kovalsky et al. |
| 2012/0078353 A1 | 3/2012 | Quadri et al. |
| 2012/0215303 A1 | 8/2012 | Quadri et al. |
| 2013/0090726 A1 | 4/2013 | Rowe et al. |
| 2013/0116779 A1 | 5/2013 | Weber |
| 2013/0211508 A1 | 8/2013 | Lane et al. |
| 2013/0226289 A1 | 8/2013 | Shaolian et al. |
| 2013/0253642 A1 | 9/2013 | Brecker |
| 2013/0261741 A1 | 10/2013 | Accola |
| 2013/0274873 A1 | 10/2013 | Delaloye et al. |
| 2013/0289718 A1 | 10/2013 | Tsukashima et al. |
| 2013/0310928 A1 | 11/2013 | Morriss et al. |
| 2013/0325114 A1 | 12/2013 | McLean et al. |
| 2014/0018915 A1 | 1/2014 | Biadillah et al. |
| 2014/0052237 A1 | 2/2014 | Lane et al. |
| 2014/0243966 A1 | 8/2014 | Garde et al. |
| 2014/0277390 A1 | 9/2014 | Ratz et al. |
| 2014/0277411 A1 | 9/2014 | Bortlein et al. |
| 2014/0277412 A1 | 9/2014 | Bortlein et al. |
| 2014/0277424 A1 | 9/2014 | Oslund |
| 2014/0277427 A1 | 9/2014 | Ratz et al. |
| 2014/0296969 A1* | 10/2014 | Tegels ................... A61F 2/2412 623/2.11 |
| 2014/0324164 A1 | 10/2014 | Gross et al. |
| 2014/0358224 A1* | 12/2014 | Tegels ................... A61L 27/54 623/2.14 |
| 2015/0127093 A1 | 5/2015 | Hosmer et al. |
| 2015/0142100 A1 | 5/2015 | Morriss et al. |
| 2015/0148896 A1* | 5/2015 | Karapetian ........... A61F 2/2427 623/2.11 |
| 2016/0120642 A1 | 5/2016 | Shaolian et al. |
| 2017/0189177 A1 | 7/2017 | Schweich, Jr. et al. |
| 2017/0266003 A1* | 9/2017 | Hammer ............... A61F 2/2436 |
| 2018/0125647 A1* | 5/2018 | Nasr ..................... A61F 2/2412 |
| 2018/0193140 A1 | 7/2018 | Weber |
| 2020/0078170 A1 | 3/2020 | Weber |
| 2020/0078171 A1 | 3/2020 | Weber |
| 2020/0093596 A1 | 3/2020 | Weber |
| 2021/0015605 A1 | 1/2021 | Bortlein et al. |

FOREIGN PATENT DOCUMENTS

| | | |
|---|---|---|
| DE | 10 2011 054 172 A1 | 3/2013 |
| WO | 2009/053497 A1 | 4/2009 |
| WO | 2009/155561 A2 | 12/2009 |
| WO | 2010/008548 A2 | 1/2010 |
| WO | 2011/111047 A2 | 9/2011 |
| WO | 2011/137531 A1 | 11/2011 |
| WO | 2013/037519 A1 | 3/2013 |
| WO | 2013/120181 A1 | 8/2013 |
| WO | 2014/080339 A1 | 5/2014 |

OTHER PUBLICATIONS

Lee et al. "Survival and recurrence after acute pulmonary embolism treated with pulmonary embolectomy or thrombolysis in New York State, 1999 to 2013," The Journal of Thoracic and Cardiovascular Surgery, vol. 155, No. 3, Mar. 2018, pp. 1084-1090.

Liang et al., "Double-crowned valved stents for off-pump mitral valve replacement," European Journal of Cardio-thoracic Surgery, vol. 28, 2005, pp. 194-199.

* cited by examiner

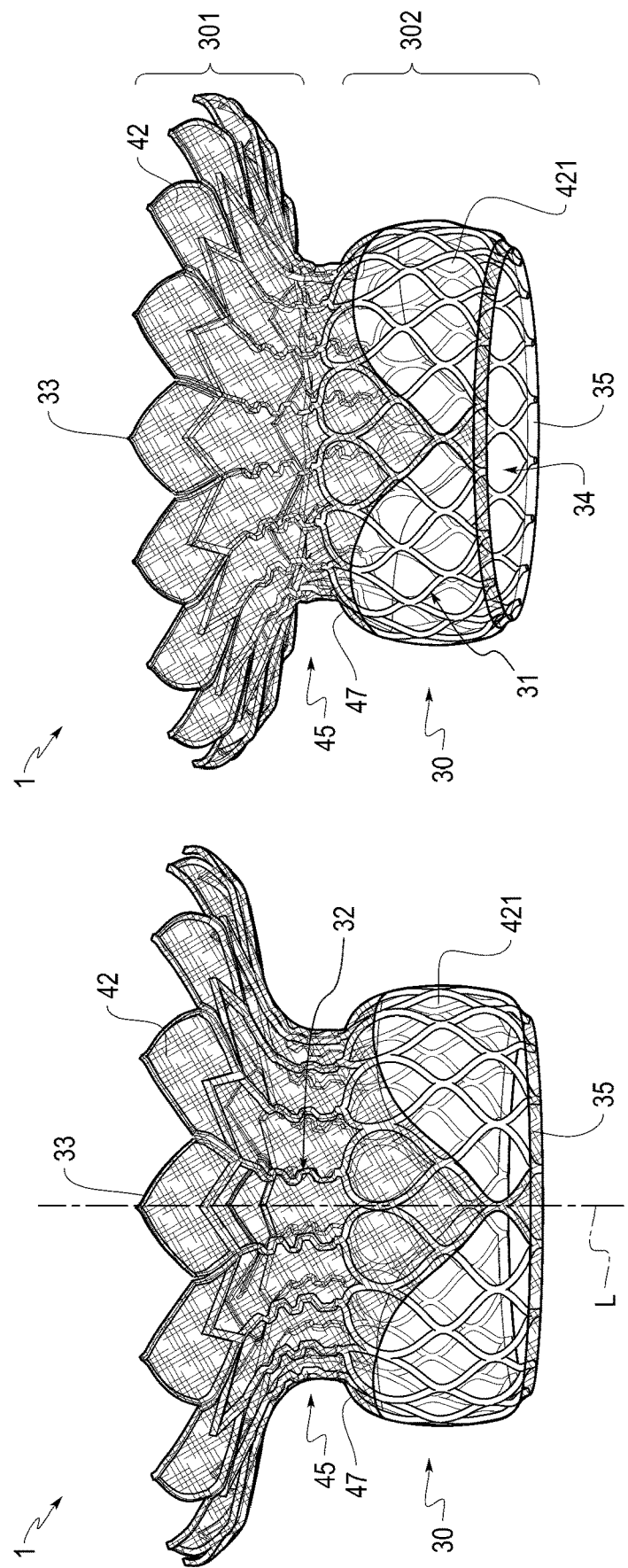

TRANSCATHETER VALVE PROSTHESIS AND METHOD FOR IMPLANTING THE SAME

This nonprovisional application claims the benefit of U.S. Provisional Application No. 63/044,534 filed Jun. 26, 2020. The entire content of the prior application is hereby incorporated herein by reference.

BACKGROUND

The heart pumps blood through the body via blood vessels of the circulatory system. The pumped blood carries oxygen and nutrients to the body, and carries metabolic waste, such as carbon dioxide, to the lungs. The heart includes four distinct chambers. The right side of the heart includes the right atrium and the right ventricle, and is responsible for receiving de-oxygenated blood from the body, and then pumping the de-oxygenated blood to the lungs in order to oxygenate the blood. The left side of the heart includes the left atrium and left ventricle, and is responsible for receiving oxygenated blood from the lungs, and then pumping the oxygenated blood to various parts of the body. Four valves regulate the movement of blood within the chambers of the heart: the aortic valve, the mitral valve, the pulmonic valve, and the tricuspid valve. These valves open and close repeatedly, and therefore, can be subject to wear and tear and other challenges that affect their performance.

Indeed, heart valve diseases affect approximately 300,000 people worldwide each year. Those diseases may include abnormal leaflet tissue, for example, excess tissue growth, tissue degradation/rupture, or tissue hardening/calcifying. Those diseases may also include abnormal tissue position through the cardiac cycle of the heart, for example, annular dilation or ventricular reshaping (e.g., valve prolapse). Such abnormal leaflet tissue and abnormal tissue position may lead to degradation in valve function including leakage/blood backflow (valve insufficiency and regurgitation) or a resistance to blood forward flow (valve stenosis).

A valve treatment procedure is an invasive or minimally invasive surgical or interventional procedure in which a patient's defective heart valve is repaired or replaced. Thus, the abnormal leaflet tissue or the abnormal tissue position may be repaired in order to restore operability of the heart valve. In a valve replacement procedure, a valve prosthesis is delivered to the patient's native heart valve without removing the patient's native heart valve. Instead, the valve prosthesis replaces the functions of the native heart valve so as to regulate blood flow through the chambers of the heart. The valve prosthesis should be implanted in a manner that avoids obstructing blood flow or disrupting the natural flow path and natural hemodynamics.

SUMMARY

Disclosed herein are a transcatheter valve prosthesis and a method for implanting the prosthesis in a heart of a patient. The prosthesis includes a tubular body coupled to a prosthetic valve. A fabric may be disposed on an outer surface of the tubular body.

The method includes partially deploying the tubular body from a catheter to a position distal of a distal edge of a native valve leaflet, and moving the catheter such that the deployed outflow end portion of the tubular body engages the distal edge of the native valve leaflet and lifts the native valve leaflet in the proximal direction towards an atrial chamber of the heart. Then, the tubular body can be fully deployed such that the native valve leaflet is captured between the outflow end portion and the inflow end portion.

BRIEF DESCRIPTION OF THE DRAWINGS

In the drawings, like reference characters generally refer to the same parts throughout the different views. The drawings are not necessarily to scale, emphasis instead generally being placed upon illustrating the principles of the invention. In the following description, various embodiments are described with reference to the following drawings, in which:

FIGS. 1A-1C schematically show a transcatheter valve prosthesis according to the disclosed embodiments.

DETAILED DESCRIPTION OF EMBODIMENTS

The following detailed description refers to the accompanying drawings that show, by way of illustration, specific details in which the disclosed embodiments may be practiced. Other embodiments may be utilized and structural and logical changes may be made without departing from the scope of the present disclosure. The various embodiments are not necessarily mutually exclusive, as some aspects of embodiments can be combined with one or more aspects of other embodiments to form additional embodiments.

Figure 2:
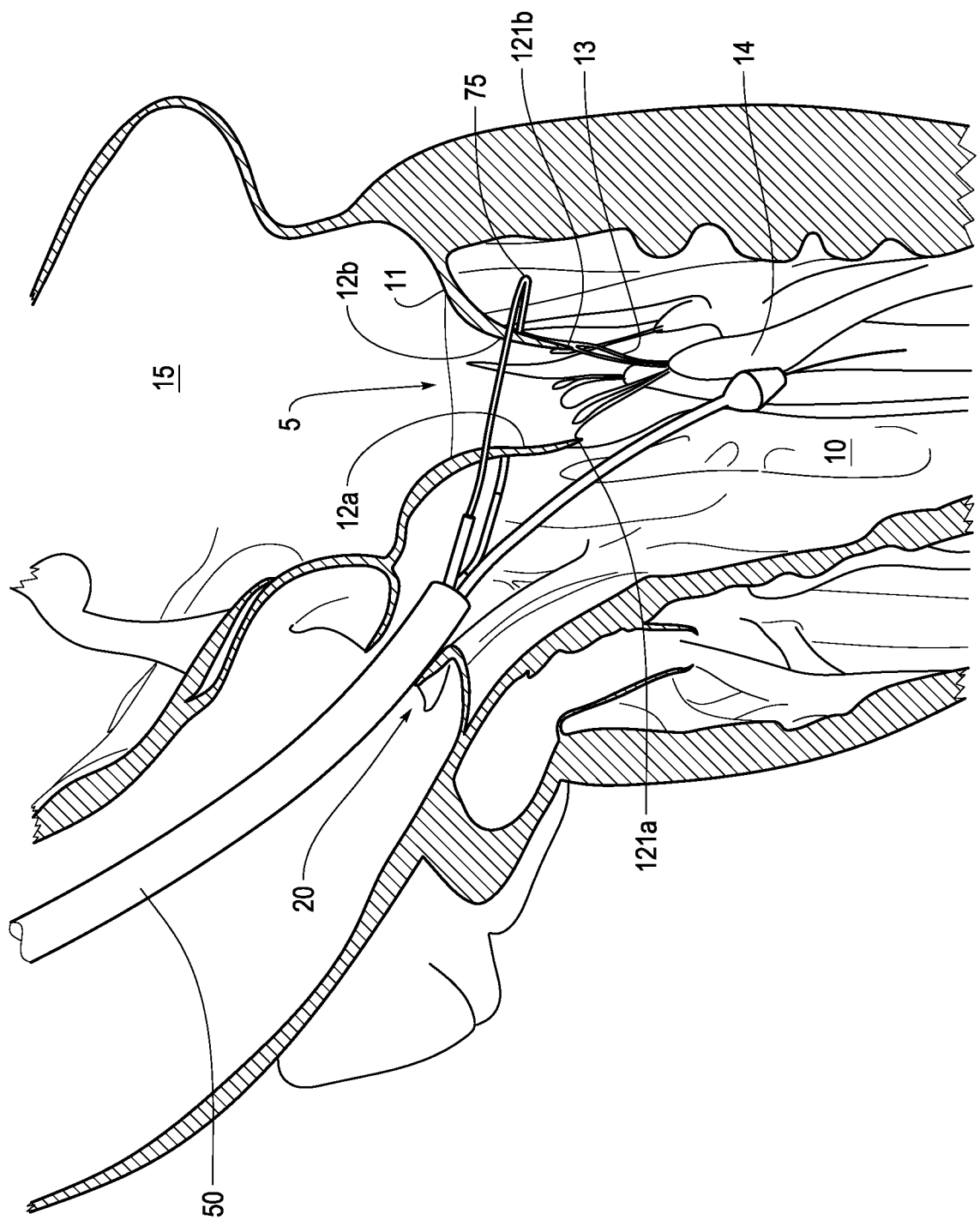
FIG. 2 schematically shows a method of delivering an elongate member to a native valve according to the disclosed embodiments.

The prosthesis and methods of implantation described herein are for functional replacement of a native atrioventricular heart valve 5, such as a native mitral valve or tricuspid valve, connecting an atrial chamber 15 with a ventricular chamber 10 (see FIG. 2). The native atrioventricular heart valve 5 (e.g., a mitral valve or a tricuspid valve) to be replaced has a generally circumferential wall structure forming a connection channel (or through opening) between the atrial 15 and ventricular 10 chambers of the heart. It includes a circumferential valve annulus 11, valve leaflets 12a, 12b for opening and closing the connection channel/through opening, a generally circumferential chord structure (chordae tendinae) 13 extending between the valve leaflets 12a, 12b and papillary muscle(s) 14, and the papillary muscle(s) 14.

In addition to functional replacement of the native valve, the disclosed prostheses and methods are designed to reduce the likelihood of partial or complete obstruction of blood flow through the left ventricular outflow tract (LVOT) or right ventricular outflow tract (RVOT). For instance, the disclosed prosthesis and methods can reduce the risk of partial or complete obstruction of blood flow from the left ventricle to the aorta or from the right ventricle to the pulmonary artery.

In transcatheter valve replacement (e.g., of the native mitral or tricuspid valve), some patients are currently screened out and are not eligible to the treatment because of the increased or prohibitive risk of obstruction of the LVOT or RVOT by the ventricular part of prosthesis (e.g., the outflow end portion). After implantation of a mitral or tricuspid valve, blood should flow from the atrial chamber (e.g., left or right atrium) through the valve to the ventricular chamber (e.g., left or right ventricle) and out through the aortic valve or pulmonic valve without obstruction. However, in some patients, blood flows from the atrial chamber through the valve, but is obstructed from flowing from the ventricular chamber to the aorta or pulmonary artery by the outflow end of a fabric-covered tubular body forming part of the prosthesis and/or is obstructed by the native valve leaflet (e.g., anterior valve leaflet). Risk factors for obstruction of the LVOT or RVOT may be related to the anatomy of the patient's native heart tissue. For example, such risk factors include septal hypertrophy or bulge, small left or right ventricular cavity size, and anterior leaflet angle or length.

The prostheses and implantation methods disclosed herein are designed to reduce the likelihood of partially or completely obstructing blood flow through the LVOT or RVOT. Even though some portions of the prosthesis (e.g., outflow end portion) are designed to be implanted in the ventricular chamber of the heart, the sub-annular or ventricular portion of the prosthesis is designed to permit blood flow there through. Additionally, the implantation methods disclosed herein are designed to lift the native valve leaflets to avoid obstruction by the native leaflets covering a sub-annular portion of the prosthesis. In some embodiments, the patient treated by the disclosed prosthesis and implantation method is at risk of obstruction of a left ventricular outflow tract or a right ventricular outflow tract by the anterior mitral valve leaflet or the anterior or septal tricuspid valve leaflet.

FIGS. 1A and 1B show an exemplary transcatheter atrioventricular valve prosthesis 1 for functional replacement of the native atrioventricular heart valve 5, such as a native mitral valve or tricuspid valve. The transcatheter valve prosthesis 1 includes a tubular body 30 having a proximal, inflow end 33 and a distal, outflow end 35 (according to the direction of blood flow when the system is implanted in a patient) extending along a longitudinal axis L. As used herein, "proximal" refers to a direction toward the inflow end 33, and "distal" refers to a direction toward the outflow end 35. The tubular body may be divided into an inflow end portion 301 and an outflow end portion 302.

Figure 7:
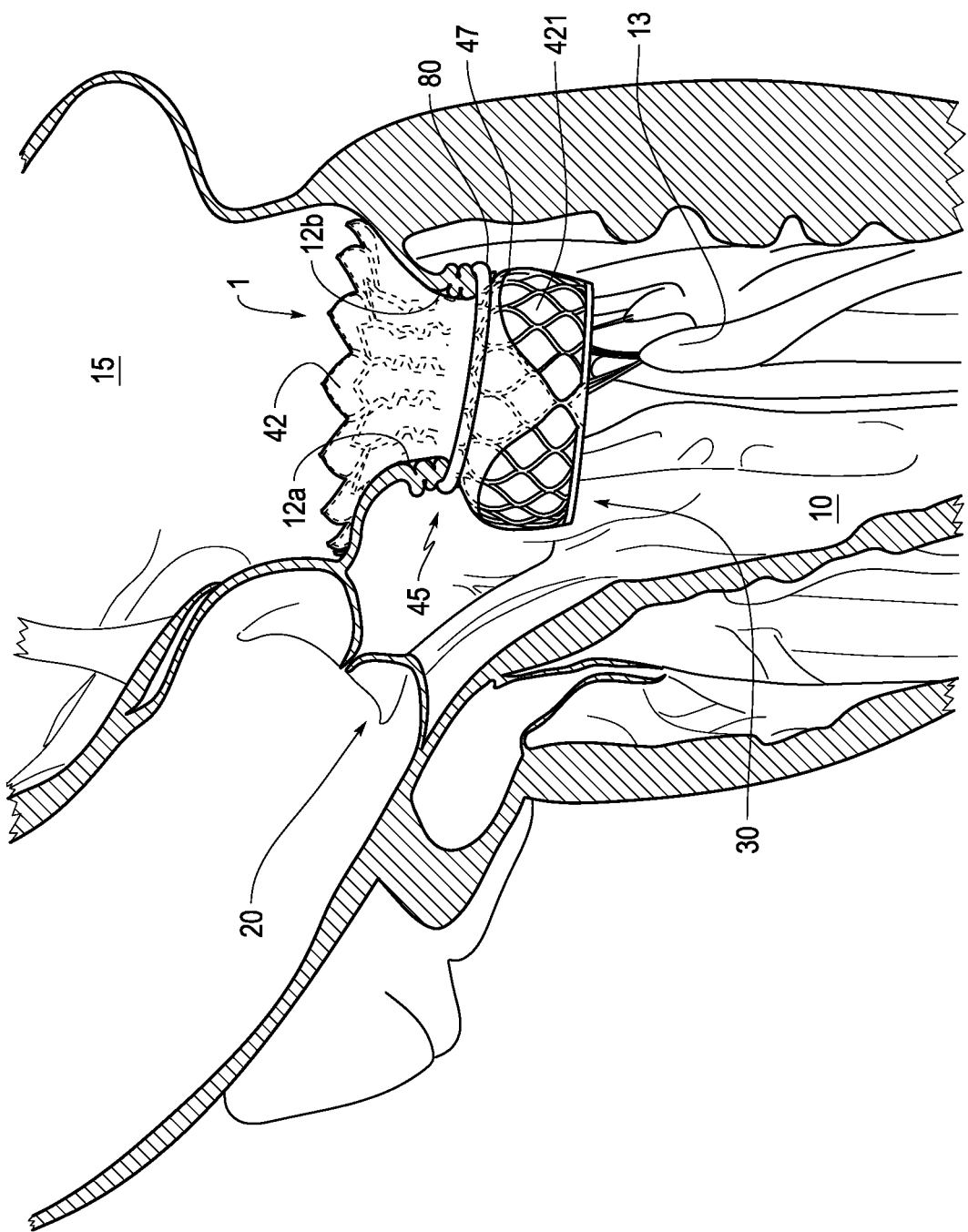
FIG. 7 schematically shows the prosthesis implanted in the native valve after the tubular body has been fully deployed according to the disclosed embodiments.

When implanted, the tubular body 30 may be disposed in the interior of the native heart valve 5 (see FIG. 7). The tubular body 30 may be radially compressible so as to facilitate approach to and insertion into native heart valve 5, e.g., using a catheter or the like, and then may be radially expandable so as to closely engage the interior or inner side of the native heart valve 5. The tubular body 30 may be radially, self-expandable, or may be balloon expandable. In the method for implanting the prosthesis 1, the outflow end portion 302 of the tubular body 30 may be radially expanded before the inflow end portion 301 is radially expanded.

Figure 1C:
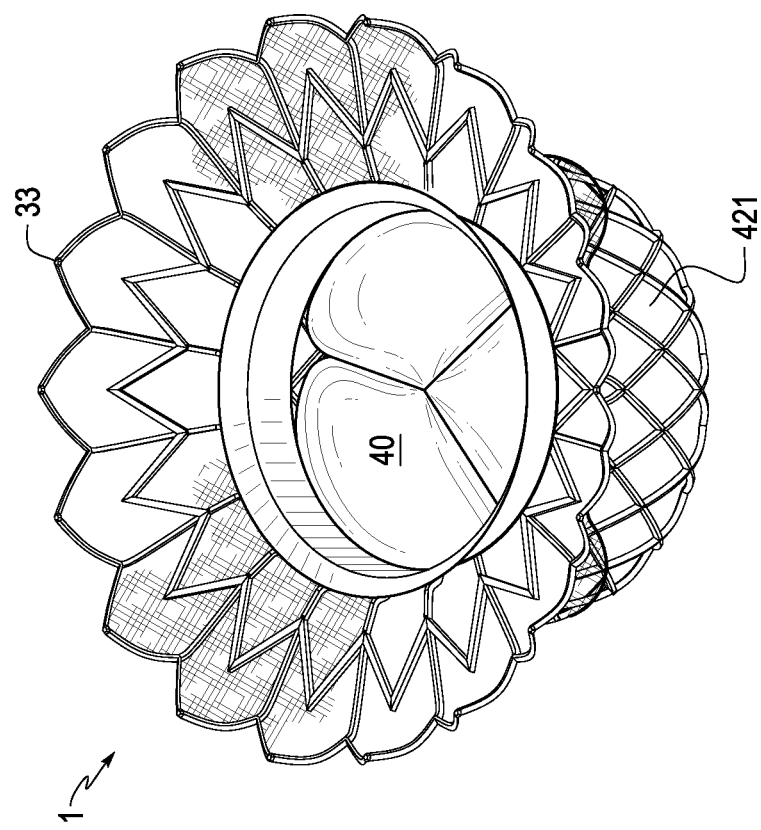

The tubular body 30 is coupled to a prosthetic heart valve 40 such that the valve 40 is arranged within a central lumen 34 of the tubular body 30, as shown in FIG. 1C. The prosthetic valve 40 is designed to serve as an artificial replacement valve for a native atrioventricular heart valve 5 (for example, a mitral or tricuspid valve). The exemplary prosthetic valve 40 shown in FIG. 1C includes three prosthetic leaflets for functional replacement of the native heart valve. The valve 40, however, is not limited to this configuration, and may include any number of leaflets, such as one, two or more leaflets. The valve can be arranged on a radially inner side of the tubular body 30 so as to be coupled to a radially inner side of one or more struts 31. The valve may be coupled to a radially inner side of the tubular body 30 at a position near a midpoint of the tubular body along the longitudinal axis L, or at a position proximate to a groove 45 formed in an outer circumference of the tubular body 30, or may be coupled to an outflow end 35 of the tubular body 30 such that the valve leaflets extend in a distal direction from the outflow end 35 of the tubular body 30. The prosthetic valve 40 may be coupled to the tubular body 30 by any suitable coupling mechanism, including, for example, sutures, adhesive, clips, metal and plastic bands, barbs, and any other suitable attachment element.

Figure 4:
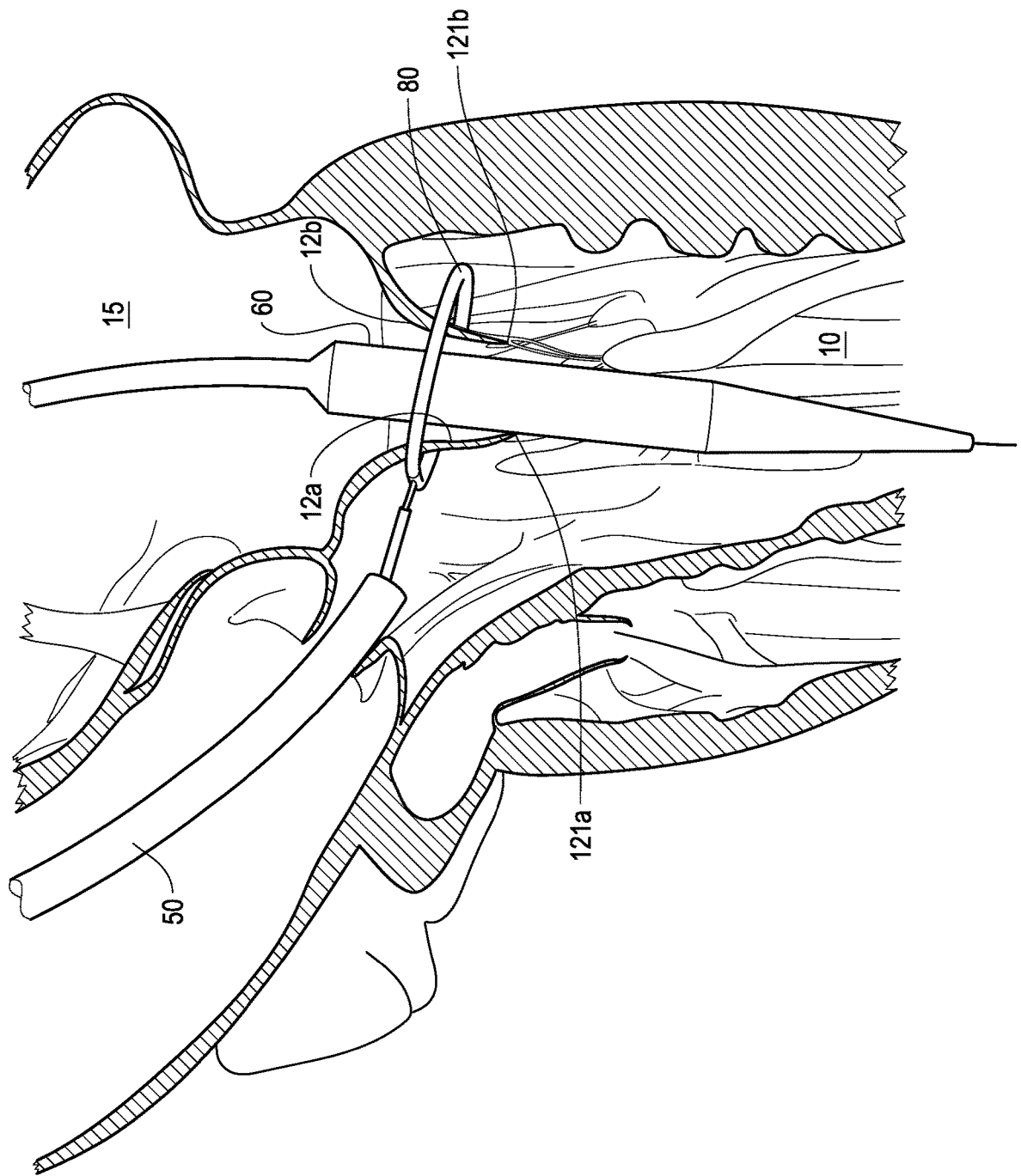
FIG. 4 schematically shows a method of delivering a catheter to the native valve over an antegrade route for implanting a tubular body including the prosthetic valve according to the disclosed embodiments.
Figure 5:
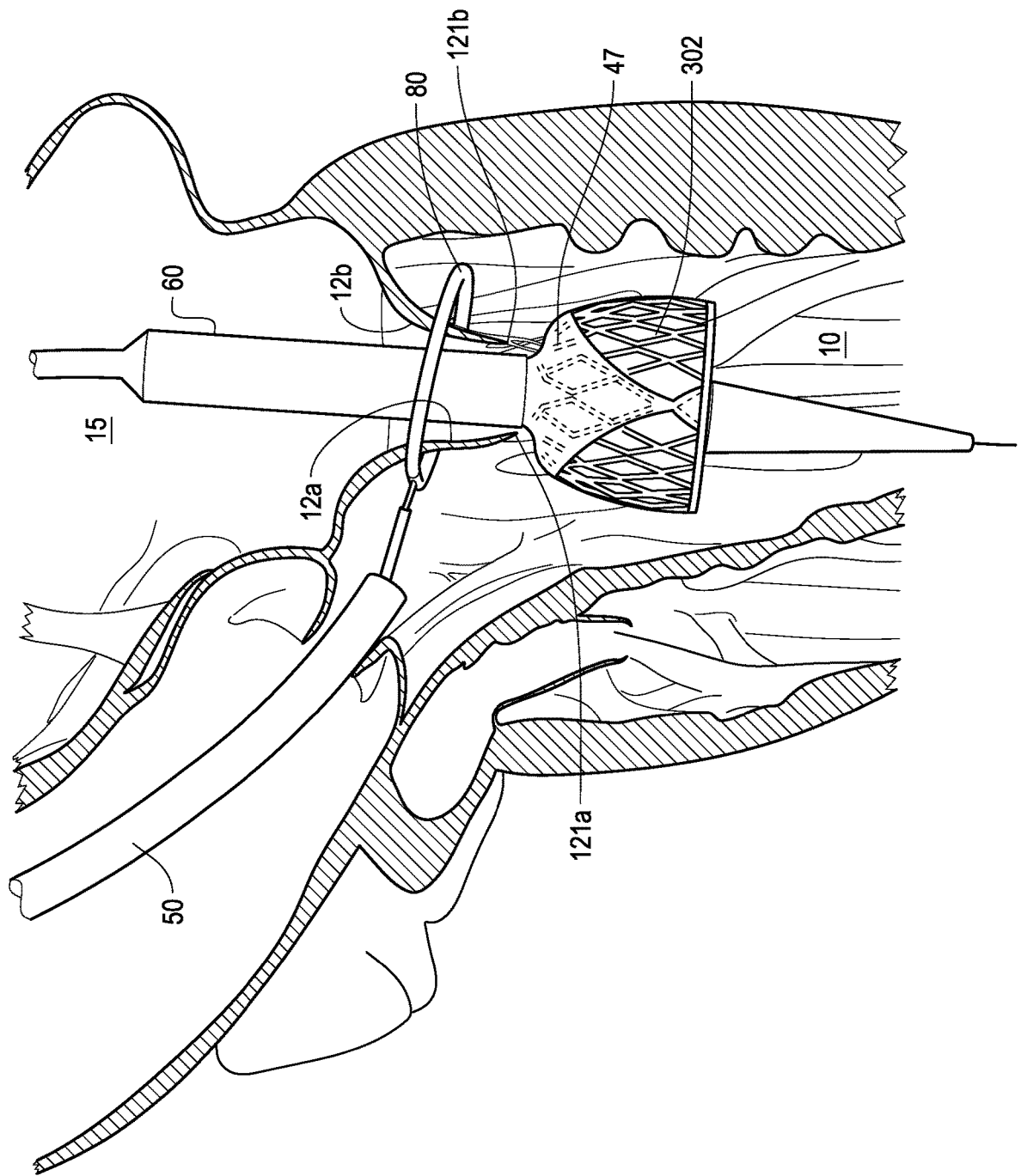
FIG. 5 schematically shows a method of partially deploying the tubular body in a ventricular chamber of the heart at a position distal of the distal edge of the native valve leaflets according to the disclosed embodiments.
Figure 6:
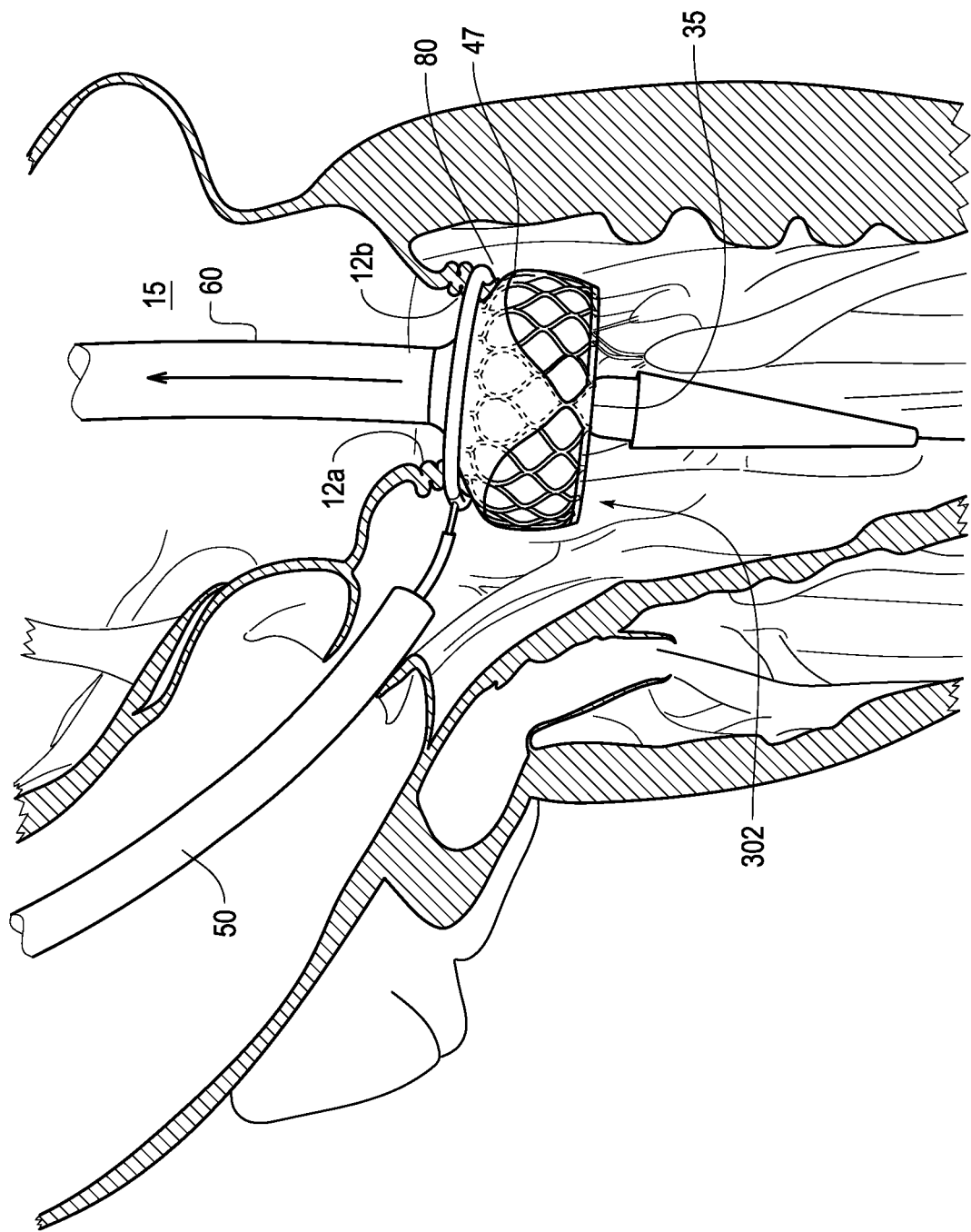
FIG. 6 schematically shows a method of moving the catheter in a proximal direction such that the partially deployed tubular body engages and lifts the native valve leaflets according to the disclosed embodiments.

The tubular body 30 may be formed of a mesh-like structure, which can be delivered within a patient via a delivery catheter 60 inserted over the antegrade route (trans-septal or trans-atrial delivery for the mitral valve, or superior/inferior vena cava delivery for the tricuspid valve) or over the retrograde route (trans-apical or through the aortic/pulmonic valve) (see FIGS. 4-6). The mesh-like structure of the tubular body 30 may include a plurality of struts 31 formed of a superalloy and/or a shape memory alloy including nickel, titanium, and/or precious metals (e.g., gold). The tubular body 30 may be formed of Nitinol or one or more polymers, such has polyvinyl-chloride, polystyrene, polypropylene, and/or another polymer. For example, the tubular body 30 may be formed of one or more bioabsorbable polymers.

As shown in FIGS. 1A and 1B, the tubular body 30 may also include flexible struts 32. Such flexible struts 32 may have an S-shape. The S-shaped struts 32 may overlap a groove 45 formed in the tubular body 30 or may be disposed on an inflow (e.g., proximal) side of the groove 45. The S-shaped struts 32 may each form a decorrelation portion that dissociates movements between inflow end 33 of the tubular body 30 and the outflow end 35 of the tubular body 30. Thus, the S-shaped struts 32 may be configured to stress and compress in reaction to movement of the inflow end 33 or the outflow end 35. Thus, because the S-shaped struts 32 stretch and/or compress movement from one end of the tubular body 30 does not translate/communicate to the other end of the tubular body 30. The S-shaped struts 32 may be disposed entirely proximal of preformed groove 45 in an inflow direction.

The tubular body 30 may be generally cylindrical in shape. As shown in FIGS. 1A and 1B, the tubular body 30 may include a groove 45 between the inflow end 33 and the outflow end 35. The inflow end portion 301 of the tubular body 30 may flare radially outward so as to have a larger outer diameter than the outflow end portion 301, as shown in FIGS. 1A and 1B. The inflow end portion 301 may have a generally conical or expanding shape along a central (longitudinal) axis L of the tubular body, with its cross-section diameter increasing from the groove 45 toward the inflow end 33. The outflow end portion 302 may be generally cylindrical. Alternatively, both of the inflow end portion 301 and the outflow end portion 302 may have a conical shape along the axis of the tubular body, with their respective cross-sectional diameters increasing from the groove 45. Additionally, the outflow end portion 302 of the tubular body 30 may include a frustoconical shape that slopes radially outward from the groove 45 toward the outflow end 35.

The outer diameter of the inflow end portion 301 may increase along a direction from the groove 45 to the inflow end 33. The inflow end portion 301 may be designed to be large enough to provide an effective paravalvular leakage seal. For example, as shown in FIG. 7, the inflow end portion 301 is designed to be disposed against a surface of a native annulus when implanted into a patient. The inflow end portion 301 may be designed to be disposed against a surface of the native annulus in an atrial chamber of the heart, e.g., the left atrium 15 of the heart or the right atrium of the heart. The outflow end portion 302 of the tubular body 30 may be substantially cylindrical, or may include a frustoconical shape that slopes radially outward from the shoulder 47. Alternatively, outflow end portion 302 of tubular body 30 may be tapered radially inward.

The cross sections of the inflow end portion 301 and outflow end portion 302 may be or contain non-circular shapes such as elliptical or D-shaped cross sections. In addition, the direction of curvature in the axial profile (seen in an axial section along the tubular body 30) between the groove 45 and the inflow end 33 and/or between the groove 45 and outflow end 35 may change (e.g., from concave curvature of the groove 45 to a convex curvature at the transition between groove 45 and the inflow end 33 or outflow end 35).

In FIGS. 1A and 1B, the groove 45 extends in a circumferential direction around the tubular body 30 between the inflow end portion 301 and the outflow end portion 302 and is open to the radial outside of the tubular body 30, but is not limited to this configuration. The circumferential groove 45 may extend around a whole circumference of the tubular body 30, as in FIGS. 1A and 1B, or may only extend partially around a circumference of the tubular body 30. The outer circumferential groove 45 may be a continuous (i.e., non-interrupted) groove, or may be an interrupted groove 45 having, for example, two or more circumferential groove portions 45 that are interrupted by areas in which no groove or recessed portion is formed. The two or more groove portions 45 may be provided on the same axial level of the tubular body 30, or may be provided on different axial levels of the tubular body 30. The circumferential groove 45 may be located at an axial distance (along axis L) from the axial ends of the tubular body 30, i.e., the groove 45 may be spaced apart in an axial direction from inflow and outflow ends 33, 35 of the tubular body 30.

The tubular body 30 may be implanted in the native valve so that the groove 45 is located at the same level of or on the ventricular side of the native annulus of a natural valve, e.g., having a distance from the natural valve annulus (see FIG. 7). That is, the groove 45 may be a sub-annular groove. The groove 45 may have a diameter that is smaller than a diameter of the natural valve annulus.

The circumferential groove 45 may be an indentation in the tubular body 30 that is recessed radially inward so as to define a shoulder 47 on an outflow side of the groove 45, as shown in FIGS. 1A and 1B. The groove 45 and/or shoulder 47 may separate the tubular body 30 into the inflow and outflow portions 301, 302. The shoulder 47 can be formed at a proximal end of the outflow end portion 302 of the tubular body (e.g., on a distal side or bottom of the groove 45). The shoulder 47 may form the largest circumference or diameter of the outflow end portion 302, or the shoulder 47 may just have a larger circumference or diameter than the groove 45. The inflow end portion 301 may have a larger circumference or diameter than the shoulder 47 and/or remainder of the outflow end portion 302. For instance, the inflow end portion 301 may have a largest circumference or diameter of the tubular body 30. Alternatively, the shoulder 47 may form a largest circumference/diameter of the tubular body 30. A deepest part of the groove 45 may form the smallest circumference or diameter of the tubular body 30.

Similar to the groove 45, the shoulder 47 may extend entirely around the circumference of the tubular body 30 or may only partially extend around the circumference of the tubular body 30. For instance, the shoulder 47 may be a continuous (i.e., non-interrupted) shoulder, or may be an interrupted shoulder 47 having, for example, two or more circumferential shoulder portions 47 that are interrupted by areas in which no shoulder portion (e.g., convex portion or bulge) is formed. The two or more circumferential shoulder portions 47 may be provided, for example, on the same axial level of the tubular body 30 or may be provided at different axial levels of the tubular body 30.

The groove and/or shoulder may be positioned at an axial height of the prosthetic leaflets of the prosthetic valve or may be positioned proximal of the prosthetic leaflets. For instance, the groove and/or shoulder may be formed in the outer surface of the tubular at an axial position at or adjacent to an axial position at which prosthetic leaflets of the valve 40 is coupled to an inner surface of the tubular body 30. Alternatively, the prosthetic valve leaflets 40 may be coupled to the tubular body 30 at a position closer to an outflow end than the groove and/or shoulder.

Figure 11:
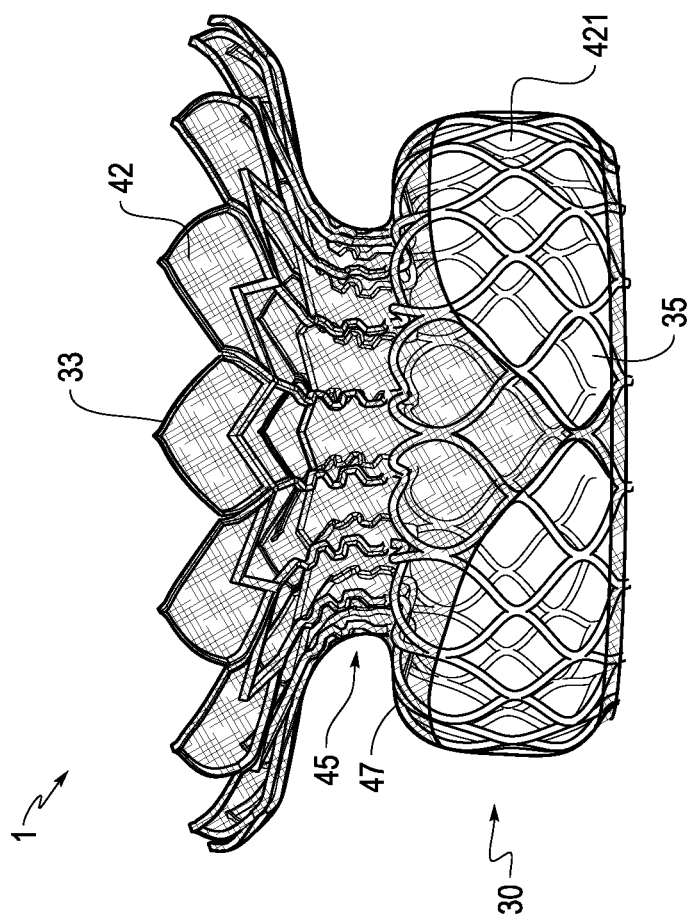
FIG. 11 schematically shows a transcatheter valve prosthesis according to the disclosed embodiments.

In FIGS. 1A and 1B, the shoulder 47 has a rounded outer surface extending toward the body of the outflow end portion 302. For instance, the shoulder 47 has curvature that opens in a direction facing the outflow end 35 of the tubular body. However, the shoulder 47 is not limited to this embodiment. For instance, the shoulder 47 may include a recess on its proximal-facing surface (e.g., facing the inflow end 33), as shown in FIG. 11. For example, a top or proximal surface of the shoulder 47 (on the inflow side) may be recessed in a direction toward the outflow end 35 of the tubular body such that a curvature of the recess opens in a direction facing the inflow end 33. The shoulder 47 recess may be slight, moderate, or severe. The circumferential outer perimeter of the shoulder 47 may be curved towards the remainder of the outflow end portion 302, as shown in FIG. 11, or may slope towards the remainder of the outflow end portion 302 at a more acute angle so as to form an edge or ridge. The recess in the shoulder 47 may help facilitate engagement with the native valve leaflets 12a, 12b. For instance, the recess in the shoulder 47 may facilitate maintaining engagement with the native valve leaflet(s) 12a, 12b when the delivery catheter is moved in the proximal direction such that the partially deployed tubular body 30 lifts the leaflets 12a, 12b in the proximal direction (e.g., toward the atrial chamber) (see FIG. 6). For example, the recess in the shoulder 47 may facilitate the rolling up, bunching up, or folding up of the leaflets 12a, 12b on the shoulder 47 and/or in the groove 45 so obstruction of the LVOT or RVOT by the leaflets 12a, 12b is avoided or reduced.

The groove 45 and/or shoulder 47 can form a leaflet engagement mechanism for engaging the native valve leaflets 12a and/or 12b during the method of implantation. For example, the shoulder 47 and/or groove 45 may be used to engage the native valve leaflets 12a, 12b during the method of implanting the prosthetic valve 1 so as to lift one or more of the native leaflets 12a, 12b in a proximal direction towards an atrial chamber of the heart, e.g., the left atrium 15 (in the case of the mitral valve) or the right atrium (in the case of the tricuspid valve). As a result, the native leaflets 12a, 12b may be in an at least partially folded up state on the shoulder 47 and/or in the groove 45. This can reduce the likelihood of blockage of the LVOT or RVOT by the native valve leaflets 12a, 12b.

Alternatively, instead of being an indentation in the tubular body 30 that is recessed radially inward so as to form a shoulder 47, the groove 45 may be a portion of the tubular body 30 from which the inflow end portion 301 flares radially outward such that the groove 45 does not define a shoulder 47. Alternatively, the tubular body 30 may not include a groove 45 at all. Instead, the tubular body 30 may be a substantially cylindrical tubular body. In such embodiments, the tubular body 30 or the prosthetic heart valve system 1 may include other means for engaging the native valve leaflets 12a, 12b (i.e., other than the groove 45 and/or shoulder 47). For instance, as described below, one or more capturing elements, such as arms 48, clips, hooks or barbs 49, tethers, clips 46, a ring 80, or the like (see FIGS. 7-10) may be used as the leaflet engagement means in lieu of or in addition to the shoulder 47 and/or groove 45. For instance, the tubular body 30 may include one or more capturing element that can be used by itself or in combination with the groove 45 and/or shoulder 47 to engage the native valve leaflets 12a, 12b so as to lift them in the proximal direction towards an atrial chamber of the heart, e.g., the left or right atrium, to reduce the likelihood of blocking the LVOT or RVOT.

As used herein, "leaflet engagement mechanism," "engagement mechanism," "leaflet engagement means," or "engagement means" may refer to any one or more of a groove, recess, indentation, slit, gash, concave portion, convex portion, shoulder (with or without a proximal-facing recess), bulge, ridge, jut, ledge, hook, barb, arm, clip, tether, fastener, catch, snare, spike, flange, or the like formed on a surface of the tubular body 30 that can facilitate engagement with the native valve leaflets during the implantation method disclosed herein and/or after the prosthesis has been implanted.

Any of the engagement mechanisms may further include an outer surface with increased friction (e.g., relative to a remainder of the prosthesis) for facilitating engagement with the native valve leaflets and retention of the native leaflets in the desired position (e.g., to avoid or reduce obstruction of the LVOT or RVOT). For instance, a part or all of the outer surface of engagement mechanism (e.g., a groove, recess, indentation, slit, gash, concave portion, convex portion, shoulder, bulge, ridge, jut, ledge, hook, barb, arm, clip, tether, fastener, catch, snare, spike, flange, or the like in the tubular body may be roughened or covered with a biocompatible adhesive or sticky pad for increased friction. The increased friction may be provided on an outer surface of the tubular body at the engagement mechanism, or the increased friction may be provided on an outer surface of a fabric covering the engagement mechanism of the tubular body.

The engagement mechanism may be positioned at an axial height of the prosthetic leaflets of the prosthetic valve or may be positioned proximal of the prosthetic leaflets. For instance, the valve leaflets of the valve 40 may be coupled to an inner surface of the tubular body at an axial position at or adjacent to an axial position at which the engagement mechanism is formed in the outer surface or coupled to the outer surface of the tubular body 30. Alternatively, the prosthetic valve leaflets 40 may be coupled to the tubular body 30 at a position closer to an outflow end than the engagement mechanism.

Figure 9:
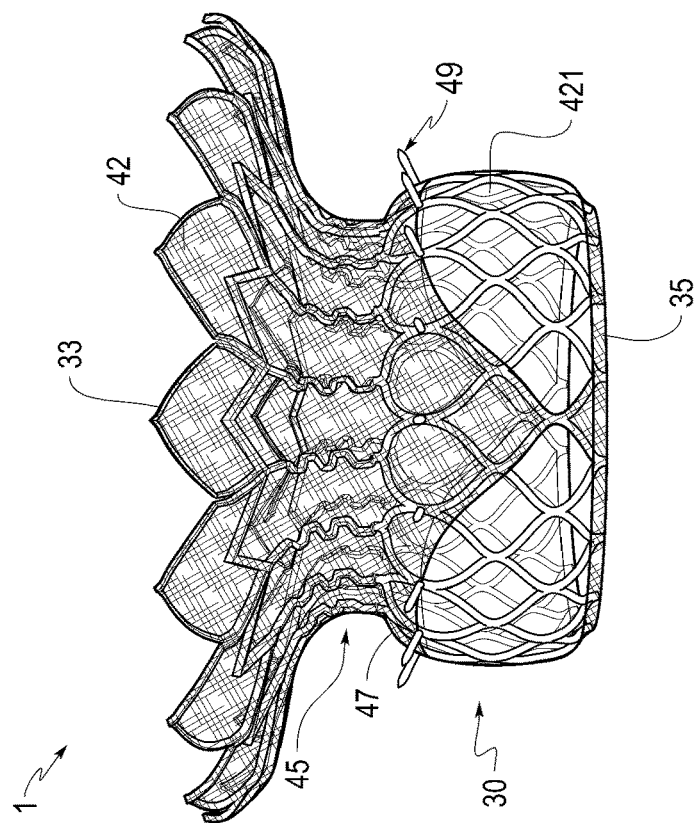
FIG. 9 schematically shows a transcatheter valve prosthesis according to the disclosed embodiments.
Figure 8:
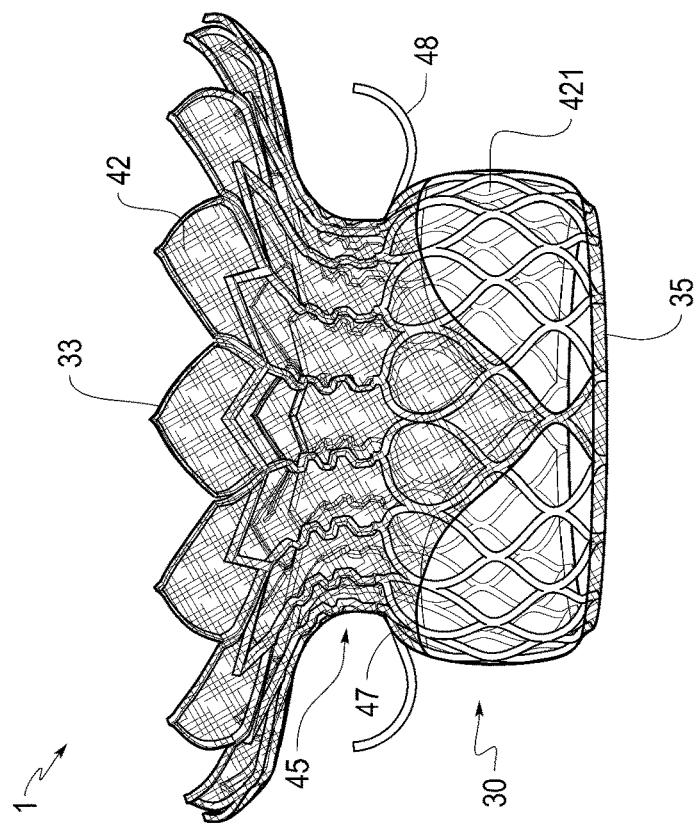
FIG. 8 schematically shows a transcatheter valve prosthesis according to the disclosed embodiments.
Figure 10:
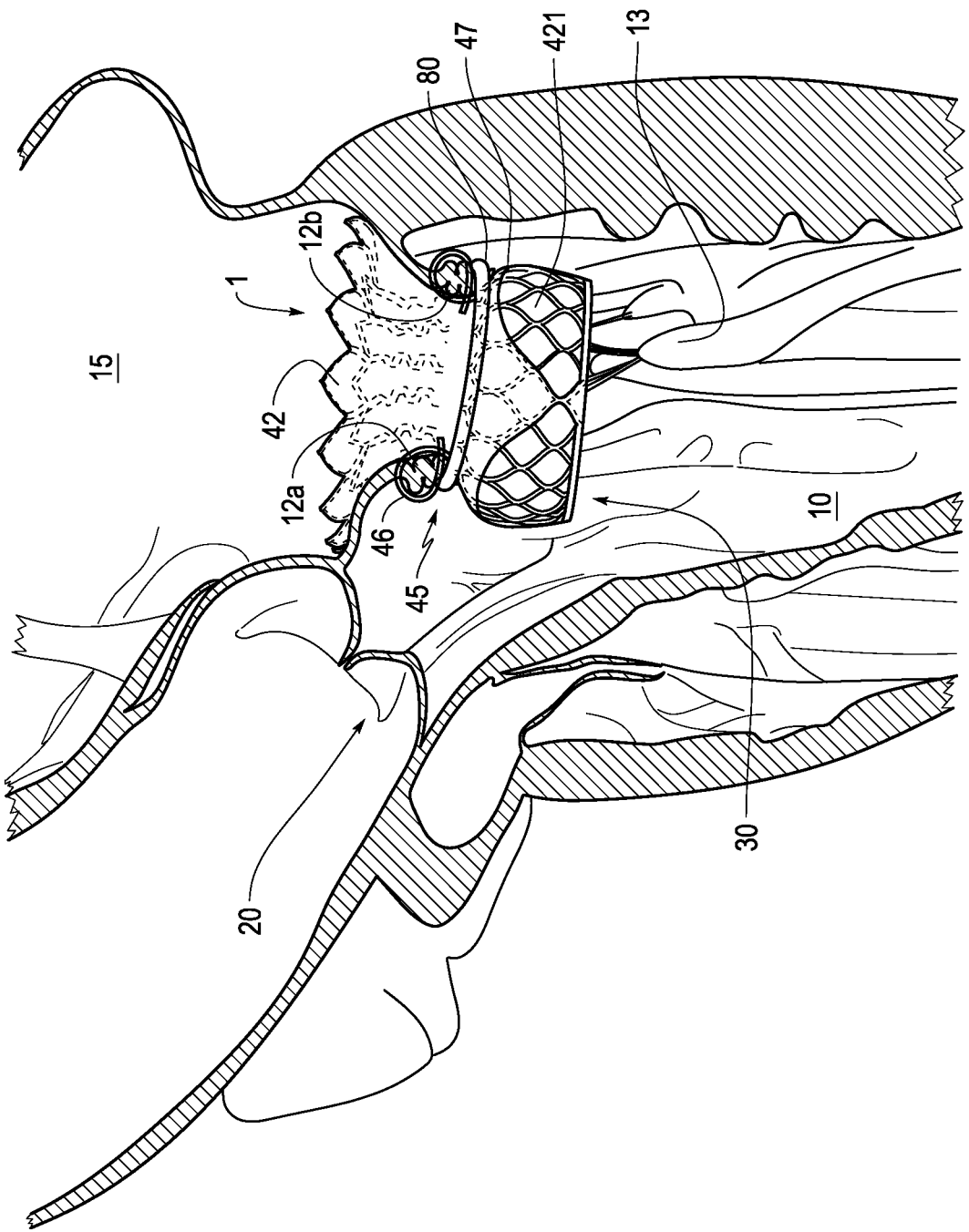
FIG. 10 schematically shows a transcatheter valve prosthesis implanted in a native valve according to the disclosed embodiments.

As discussed above, FIGS. 1A and 1B show an exemplary tubular body in which the leaflet engagement mechanism is a groove 45 and/or shoulder 47 formed in the tubular body 30. FIGS. 8-10 show non-limiting examples of other engagement mechanisms. For example, in FIG. 8, the tubular body 30 further includes arms 48 extending from the outflow end portion 302. After implantation of the tubular body 30 in the native valve 5, the arms 48 may extend around an outer surface of the native valve leaflets 12a, 12b such that the native leaflets 12a, 12b are sandwiched between the arms 48 and an outer surface of the tubular body 30. During the implantation method, the tubular body 30 may be partially deployed in which the outflow end portion 302, but not the inflow end portion 301, has been deployed from the delivery catheter (see FIGS. 5 and 6). The arms 48 or some of the arms 48, which may be coupled to the outflow end portion 302 may likewise be deployed such that when the outflow end portion 302 is moved in the proximal direction (e.g., from the ventricular chamber in a direction towards the atrial chamber), the arms 48 help capture the native valve leaflets 12a, 12b so as to lift the native valve leaflets 12a, 12b (or at least one native leaflet) in the proximal direction. This can avoid or reduce obstruction of the LVOT or RVOT and thus permit blood flow from the ventricular chamber to the aorta and/or pulmonary artery.

The arms 48 may be curved in a proximal direction (i.e., in a direction towards in the inflow end 33 of the tubular body), as shown in FIG. 8, or may extend substantially linearly so as to project radially outward or so as to be inclined in a direction towards the inflow end 33. Alternatively, the arms 48 may extend in a substantially axial direction (e.g., substantially parallel to the longitudinal axis L of the tubular body 30). The arms 48 may extend from a first end coupled to an outer surface of the tubular body 30 to a second, free end, as shown in FIG. 8. In other words, second, free end may be unattached to the tubular body 30, and the arms 48 may terminate at the second free end. Alternatively, both ends of the arms 48 may be coupled to an outer surface of the tubular body 30 so as to form a loop. For instance, a first end of the arms 48 may be coupled to an outer surface of the tubular body 30 at a first position and a second end may be coupled to an outer surface of the tubular body 30 at a second position spaced in the circumferential direction from the first position. The loop may project radially outward from the outer surface of the tubular body so as to be inclined in a direction towards the inflow end 33.

The arms 48 may be attached to the tubular body at the outflow end portion 302, as shown in FIG. 8. For instance, the arms may be coupled to a proximal side of the outflow end portion 302, for example, near the groove 45 and/or shoulder 47, as shown in FIG. 8. Alternatively, the arms 48 may be coupled to an intermediate portion of the outflow end portion 302 or may be coupled to or near the outflow end 35 of the tubular body 30.

The tubular body 30 may additionally or alternatively include arms 48 coupled to the inflow end portion 301 of the tubular body (not illustrated). The arms 48 coupled to the inflow end portion 301 may project radially outwardly from the outer surface of the inflow end portion 301 so as to extend in the radial direction or may be inclined in a direction toward the outflow end 35. Alternatively, the arms 48 may extend substantially axially (e.g., substantially parallel to the longitudinal axis L of the tubular body 30). The arms 48 coupled to the inflow end portion 301 may extend from a first end to a second free end or may have both ends coupled to the tubular body 30 in the same manner described above for the arms 48 coupled to the outflow end portion 302.

The tubular body 30 may include first and second sets of arms 48 that respectively extend from the outflow end portion 302 and the inflow end portion 301. The first set of arms 48 may extend from the outflow end portion 302 in a direction towards the second set of arms 48 extending from the inflow end portion 301. The first and/or second set of arms 48 may extend so as to at least partially or completely overlap the groove 45 in the radial direction.

The arms 48 may further include barbs or hooks (e.g., at the second, free ends) for penetrating the native heart tissue, such as the native leaflets 12a, 12b. Alternatively, the arms 48 may include blunt, flat, or rounded free ends so as to not penetrate the native heart tissue, e.g., to avoid damaging the native heart tissue.

The tubular body 30 may include one or more arms 48. For example, the tubular body may include two arms 48 on opposite sides of the tubular body for engaging the anterior and posterior leaflets 12a, 12b when implanted. Alternatively, in the case of functionally replacing the native tricuspid valve (with three valve leaflets), the tubular body 30 may include three arms 48 spaced for engaging the three native valve leaflets. Alternatively, the tubular body 30 may only include a single arm 48 positioned for engaging the native anterior leaflet 12a of the mitral or tricuspid valve so as to reduce or avoid obstruction of blood flow from the ventricular chamber to the aorta or pulmonary artery by the anterior leaflet 12a. In yet another embodiment, the tubular body 30 may include a plurality of arms 48 spaced at equal or non-equal intervals around the circumference of the tubular body.

The arms 48 may be covered by the fabric 42 disposed on an outer surface of the tubular body 30 so as to form a pocket for capturing the native valve leaflets 12a, 12b. Alternatively, the arms 48 may project through the fabric 42 or may be otherwise uncovered by the fabric 42.

With reference to FIG. 9, the tubular body may alternatively or additionally include hooks or barbs 49 as an engagement mechanism to facilitate capture and retention of the native valve leaflet(s) 12a, 12b. For example, the hooks or barbs 49 may jut out from an outer surface of the outflow end portion 302 of the tubular body 30 to facilitate capture of the native leaflets 12a, 12b on the shoulder 47 and/or in the groove 45 of the tubular body 30. The hooks or barbs 49 may be designed to penetrate the native valve leaflets 12a, 12b to better facilitate retention thereof on the engagement means. The hooks or barbs 49 may be formed on a proximal end side of the outflow end portion 302, for example, near the shoulder 47 or groove 45, as shown in FIG. 9, or may be formed closer to or at the outflow end 35 of the tubular body 30. The inflow end portion 301 may alternatively or additionally include hooks or barbs 49 projecting from an outer surface thereof to further secure the native valve leaflets 12a, 12b in position with respect to the tubular body 30. The tubular body 30 may include one, two, three, four, five, or more hooks or barbs 49, and the hooks or barbs 49 may be equally or non-equally spaced around an outer circumference of the tubular body 30.

With reference to FIG. 10, the tubular body may alternatively or additionally include clips 46 as an engagement mechanism to facilitate capture and retention of the native valve leaflet(s) 12a, 12b. For example, the clips 46 may be provided on an outer surface of the outflow end portion 302 of the tubular body 30 to facilitate capture of the native leaflets 12a, 12b on the shoulder 47 and/or in the groove 45 of the tubular body 30. The clips 46 may be designed to clip to the native valve leaflets 12a, 12b to better facilitate retention thereof on the engagement means. The clips 46 may be formed on a proximal end side of the outflow end portion 302, for example, near the shoulder 47 or groove 45, as shown in FIG. 10, or may be formed closer to or at the outflow end 35 of the tubular body 30. The inflow end portion 301 may alternatively or additionally include clips 46 provided on an outer surface thereof to further secure the native valve leaflets 12a, 12b in position with respect to the tubular body 30. The tubular body 30 may include one, two, three, four, five, or more clips 46, and the clips 46 may be equally or non-equally spaced around an outer circumference of the tubular body 30.

The transcatheter valve prosthesis 1 may include a fabric 42 disposed at least partially around the tubular body 30. The fabric 42 can function as a buffer to limit erosion in the contact areas of the native anatomy or as a matrix favoring native tissue ingrowth or as a sealing member to occlude or fill gaps between the perimeter of a tubular body 30 and the native valve annulus 11 and leaflets 12a, 12b, thereby reducing, minimizing, or eliminating leaks there-through. As shown in FIGS. 1A, 1B, and 7, the fabric 42 is disposed on an outer surface of tubular body 30 and can block blood flow around the outer perimeter of the tubular body 30, thereby minimizing and/or eliminating any paravalvular leakage at the implantation site. When the prosthesis 1 is implanted in the native valve, the fabric 42 may extend from an inflow side of the native valve annulus to an outflow side of the native valve. The fabric 42 may extend from the inflow end 33 of the tubular body 30 to the outflow end 35 of the tubular body 30, and may extend entirely around the circumference of the tubular body 30. The fabric 42 may be disposed within the groove 45 such that the fabric 42 follows the contours of the groove 45, as shown in FIGS. 1A and 1B. The fabric 42 may be slack or tightly disposed on the tubular body 30. An outer surface of the fabric 42 may include portions that have increased friction (e.g., roughen portions, portions with a biocompatible adhesive or sticky pads), for example, relative to a remainder of the fabric 42 for facilitating engagement and capture of the native leaflets 12a, 12b by the engagement means, as discussed above.

When the tubular body 30 includes an engagement mechanism, such as arms 48, the fabric 42 may extend over a free end of the arms 49. For example, the arms 48 may project from a position near the shoulder 47, and the fabric 42 may extend from the inflow end portion 301 over the groove 45 and/or shoulder 47 and over a free end of the arms 48. The fabric 42 may further extend in the distal direction to a position near the attachment of the arms 48 to the tubular body 30 or may terminate just below (e.g. distal of) the free end of the arms 48. In such embodiments, a pocket or channel may be formed by the fabric 42 extending over the free end of the arms 48 in between the arms 48 and the outer surface of the tubular body 30, e.g., an outer surface of the groove 45 and/or shoulder 47. The pocket may further facilitate engagement and retention of the native valve leaflets 12a, 12b on the engagement means.

As shown in FIGS. 1A and 1B, the fabric 42 may include one or more lateral openings 421 arranged at the outflow end portion 302 of the tubular body 30 such that at least a portion of the outflow end portion 302 is uncovered by the fabric 42. The lateral openings 421 can permit blood flow through the outflow end portion 302. This can reduce the likelihood of LVOT or RVOT obstruction. In FIGS. 1A and 1B, the fabric 42 includes two lateral openings 421 arranged at the outflow end portion 302 of the tubular body 30. However, the fabric 42 may include only one lateral opening 421, or may include more than two lateral openings 421, such as three, four, five, or more lateral openings 421. For instance, at least one lateral opening 421 in the fabric 42 is designed to be arranged on a side of the anterior mitral valve leaflet 12a or anterior or septal tricuspid valve leaflet when the prosthesis 1 is implanted in the native valve 5. This can facilitate blood flow from the left ventricle 10 to the aorta 20 (in the case of a prosthetic mitral valve) or can facilitate blood flow from the right ventricle to the pulmonary artery (in the case of a prosthetic tricuspid valve), and thereby prevent obstruction of the LVOT or RVOT. Indeed, by virtue of the one or more lateral openings 421, a situation where the outflow end portion 302 of the tubular body 30 partially or completely blocks the LVOT or RVOT can be avoided.

In FIGS. 1A and 1B, the lateral openings 421 have a semicircle shape with the fabric 42 forming a border on the outflow end 35 of the tubular body. However, the lateral opening(s) 421 are not limited to this configuration, and the lateral opening(s) 421 may have any suitable shape or size. For example, the lateral openings 421 may have a circular, elliptical, square, triangular, rectangular, semicircular, quarter circle, star, diamond, parallelogram, polygon, or any other suitable shape. The entire or most of the outflow end portion 302 may be uncovered by the fabric 42. For example, the lateral opening 421 may start at the groove 45 or shoulder 47 or just distal of the groove 45 or shoulder 47 and extend all the way or mostly to the outflow end 35. The lateral opening 421 may be provided entirely or partially around the circumference the outflow end portion 302. The lateral openings 421 may extend all the way to the outflow end 35 such that the outflow end 35 is partially or entirely uncovered by the fabric 42.

The fabric 42 covering the inflow end portion 301 may also include one or more lateral openings 421. The lateral opening(s) 421 may have any of the configurations discussed above.

When one or more grooves 45 extend only partially around the circumference of the tubular body 30 (e.g., when the tubular body includes an interrupted groove that is interrupted by areas in which no groove or recessed portion is formed), the groove 45 (e.g., recessed portion) may be formed on a side of the tubular body 30 where one or more lateral openings 421 are present. For instance, the partial circumference groove 45 or recessed portion may be substantially aligned with a lateral opening 421 in the fabric 42 or may at least partially overlap a lateral opening 421 in the fabric 42 in the axial direction (along axis L) of the tubular body 30. The partially circumference groove 45 (e.g., recessed portion) may thus form a partially circumferential shoulder 47 that is aligned with or at least partially overlaps a lateral opening 421 in the fabric 42 in the axial L direction of the tubular body 30. The tubular body 30 may be implanted inside the native mitral or tricuspid valve 5 such that at least one lateral opening 421, at least one groove (e.g., recessed) portion 45, and at least one shoulder 47 portion are disposed so as to face in a direction of the anterior leaflet and/or the aortic valve (in the case of the mitral valve) or the pulmonic valve (in the case of the tricuspid valve).

As a result, the leaflet engagement mechanism, including the groove portion 45 and/or the shoulder portion 47, can engage the native anterior leaflet 12a of the mitral or tricuspid valve 5 so as to lift the native leaflet 12a in the proximal direction (e.g., toward the atrial chamber) to avoid obstruction of the LVOT or RVOT by the native leaflet 12a. Obstruction of the opening(s) 421 in the fabric 42 on the anterior side can be avoided or reduced so as to permit blood flow there through towards the aortic valve (in the case of the mitral valve) or the pulmonic valve (in the case of the tricuspid valve) to further reduce or avoid obstruction of the LVOT or RVOT.

The fabric 42 may include one or more segments of material. For instance, the fabric 42 may include one segment of material that completely or partially circumscribes the tubular body 30. Alternatively, the fabric 42 may include multiple segments, for example, two, four, or six segments. The segments may be overlapping or may be spaced apart so as to provide gaps between adjacent segments. The gaps between adjacent segments may provide the lateral openings 421 for facilitating blood flow through the outflow end portion 302 of the tubular body 30. The fabric 42 may be continuous with, for example, liner (not shown) disposed on an inner surface of the tubular body 30. The fabric 42 may include one layer of material or multiple layers of materials.

Suitable materials for the fabric include, but are not limited to, a low-porosity woven fabric, such as a polyester, DACRON® fabric, or other PTFE graft material, or the fabric 42 may include pericardial tissue, and/or a metal mesh material (e.g., a metal mesh formed of Nitinol). Porous materials can provide a medium for tissue ingrowth, and bioabsorbable materials and/or polyurethane foam with low density and optimal porosity promote sealing of the prosthesis 1 to the anatomy. Woven or knit materials can also provide a medium for tissue ingrowth and have the ability to stretch to conform to a curved surface.

The fabric 42 may be attached to tubular body 30 through any known securing mechanism. For example, the fabric 42 and the tubular body 30 may be secured through an adhesive, sutures, clips, barbs, metal or plastic bands, or any other suitable coupling element. The fabric 42 may be configured to assume a deployed, expanded configuration and a contracted, reduced configuration with the tubular body 30. Thus, the fabric 42 may be expanded and contracted based on the state of the tubular body 30.

The prosthesis 1 may further include a support member 80 to further secure the tubular body in the native valve and facilitate engagement with the native valve leaflets (see FIG. 7). The support member 80 can be an elongate member that is introduced around the native valve leaflets 12a, 12b so as to form a ring around the native valve leaflets 12a, 12b. The support member 80 can help secure the tubular body 30 to the anatomy of the native heart valve 5 to prevent migration of the tubular body 50. For example, the native valve leaflets 12a, 12b may be held in between an outer surface of the tubular body 80 and the support member 80 by a clamping, pinching, frictional, or interference fit. For example, the native valve leaflets 12a, 12b may be pinched or clamped between the support member 80 and the outer surface of the tubular body 30, or the native valve leaflets 12a, 12b may be held between the outer surface of the tubular body 30 and the support member 80 by a frictional or interference fit. The support member 80 may help secure the native valve leaflets 12a, 12b in the groove 45 of the tubular body 30 in a folded up or bunched up state (e.g., in embodiments where the tubular body 30 includes a groove 45). The native valve leaflets 12a, 12b may be held in the groove 45 by an interference, frictional, clamping, or pinching fit. The support member 80 may be a separate member from the tubular body 30 and may be introduced into the native valve separately from the tubular body 30.

The support member 80 may comprise a tubular structure having a longitudinal axis that may be arranged so as to extend in the circumferential groove 45 in a circumferential direction of the tubular body 30. The support member 80 may be in contact with the groove shoulder 47 of the circumferential groove 45. The support member 80 may extend around a whole circumference of the tubular body 30 or only partially around the tubular body 30. The clamping member 80 may extend, e.g., around an angle of 10 to 30 degrees or any other angle in the circumferential groove 45. The clamping member 80 may extend around the whole circumference of groove 45, e.g., around 360 degrees.

Thus, the support member 80 may trap or clamp portions of native valve leaflets 12a, 12b in preformed groove 45 or against a surface of the tubular body 30. This may help secure the tubular body 30 in a patient. The support member 80 can be introduced around the native valve leaflets 12a, 12b either before or after the tubular body 30 has been introduced inside the native heart valve 5. The support member 80 may include an outer surface with increased friction for facilitating engagement with the native valve leaflets and retention of the native leaflets in the desired position (e.g., to avoid or reduce obstruction of the LVOT or RVOT. For instance, an outer surface of the support member 80 may be roughened, or provided with a biocompatible adhesive or sticky pad to increase friction for better retention of the native valve leaflets. Alternatively, a fabric, such as that discussed above, may cover all or part of the support member 80. An outer surface of the fabric may be provided with increased friction for the same reason.

The support member 80 may include a full or partial loop. Additionally, the support member 80 may be moved around the tubular body 30 after the tubular body 30 is fully expanded or when the tubular body 30 is only partially expanded. The support member 80 may be loosely disposed within the preformed groove 45 such that an interference fit between the trapping member support member 80 and the preformed groove 45 secures the tubular body 30 in place. Alternatively, the support member 80 may clamp or pinch the native valve leaflets in the groove 45 or otherwise against an outer surface of the tubular body 30 to secure the tubule body in the native valve. Thus, the support member 80 may serve to anchor the valve prosthesis 1 within the patient. In other embodiments, the support member 80 may exert an inward, radial force on the tubular body 30 in order to anchor valve prosthesis 1 within the patient. Alternatively or additionally, the support member 80 may exert a frictional force on the native valve leaflets 12a, 12b.

The support member 80 may include a delivery configuration within a delivery catheter and a deployment configuration in which the support member 80 is deployed from the delivery catheter. In embodiments, the support member 80 may be biased to the deployment configuration. For example, the support member 80 may include a shape-memory alloy such as a Nitinol or a Nitinol-based alloy. Alternatively, the support member 80 may be introduced over an elongate member 75, such as a guidewire, as discussed below. The elongate member 75 may be removed from the patient after implanting the prosthesis 1 in the native heart. Alternatively, the elongate member 75 may be part of the prosthesis and thus may remain in the patient after implantation. The support member 80 and/or elongate member 75 can be introduced around the native valve leaflets 12a, 12b either before or after the tubular body 30 has been introduced inside the native heart valve 5.

The ring formed by the support member 80 after the prosthesis has been implanted in the native heart may be larger in circumference than a groove 45 in the tubular body 30, but smaller in circumference than a shoulder 47 in the tubular body 30. The support member 80 may have a cross-sectional diameter transverse to its longitudinal axis. The cross-sectional diameter may be selectively changeable to a larger or smaller diameter. That is, the support member 80 may be compressible (so as to be insertable via a catheter) and/or expandable (for example, re-expandable after being compressed) in a radial direction of its diameter, whereby the inner and outer circumferences of the support member 80 are correspondingly decreased/expanded and expanded/decreased, respectively, in a radial direction of the tubular body 30. The cross sectional diameter of the support member 80 may be smaller than the cross sectional diameter of the tubular body 30. In embodiments, the diameter of the support member 80 may be smaller than the width of the outer circumferential groove 45. The support member 80 may be provided in order to clamp heart tissue that is located inside the circumferential groove 45 outwards in a direction from the axis L towards the pluralities of projections 50, 55.

All embodiments of valve prosthesis 1 may include positioning and/or orientation devices (not shown) to facilitate relative and/or absolute positioning of the tubular body 30. These devices may include passive markers that are fixedly attached to the tubular body 30. The passive markers may be made from materials different from the materials of the tubular body 30 in order to improve contrast during medical imaging, e.g., using magnetic resonance or X-ray based imaging techniques. The passive markers may, for example, be made of highly radio-opaque materials thereby allowing one to precisely acquire the relative and/or absolute position of the components of valve prosthesis 1 with respect to the patient's body.

The prosthesis 1 can be delivered and deployed within the left ventricle of the heart to limit or prevent LVOT obstruction or can be delivered and deployed within the right ventricle of the heart to limit or prevent RVOT obstruction. With the prosthesis 1 implanted and radially expanded within native mitral or tricuspid valve, the tubular body 30 creates and/or expands a passageway in the LVOT or RVOT, and limits or prevents a native leaflet 12a, 12b (e.g., native anterior mitral leaflet or native anterior or septal tricuspid leaflet) from occluding the passageway. For instance, blood can flow through the lateral openings 421 in the fabric 42 at the outflow end portion 302 of the tubular body 30. Additionally, the leaflet engagement mechanism and implantation technique help move at least one of the leaflets (e.g., at least the anterior leaflet) in the proximal direction (e.g., towards the left or right atrium) so as to reduce or eliminate LVOT or RVOT obstruction by the native valve leaflets (e.g., anterior leaflet).

Figure 3:
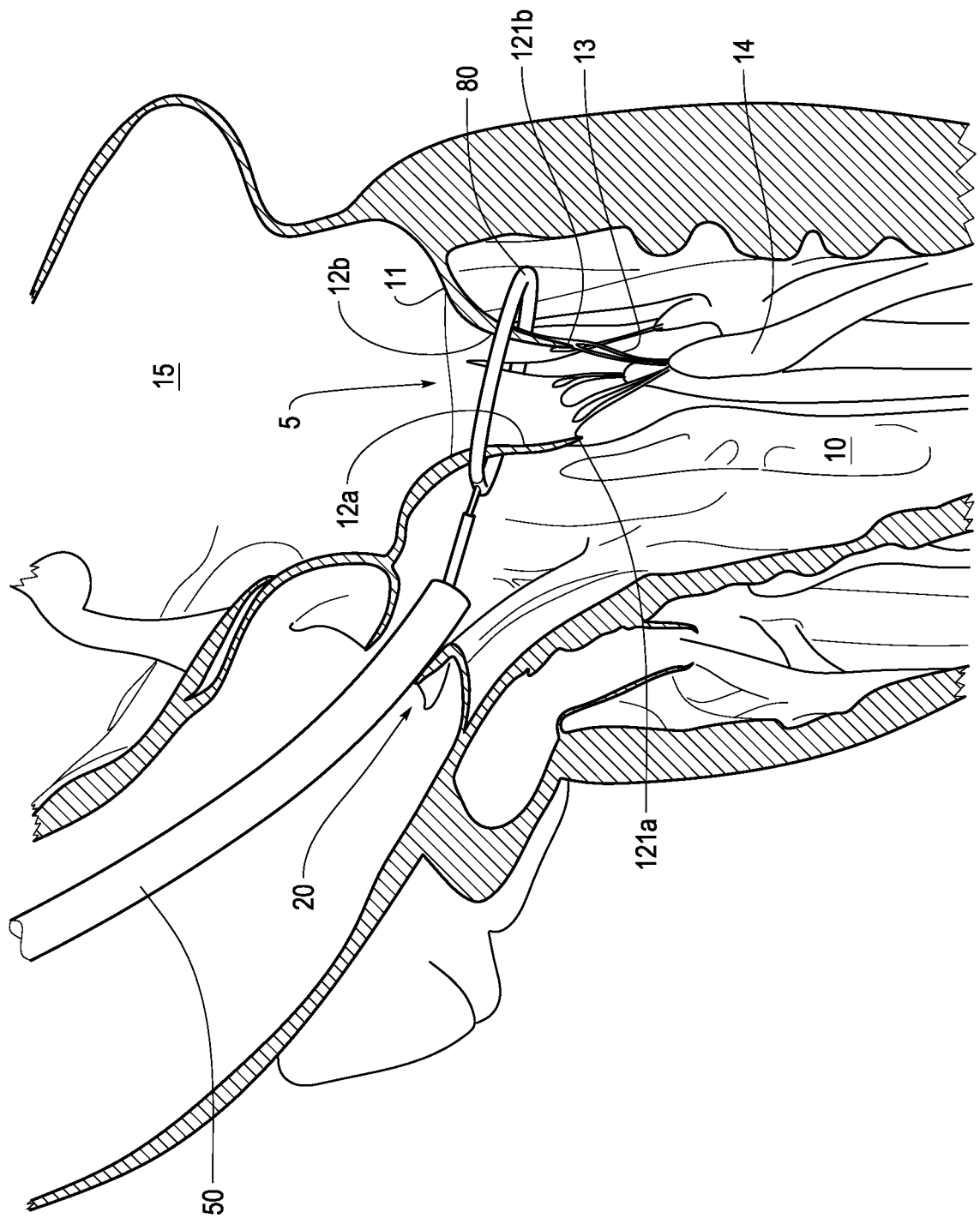
FIG. 3 schematically shows a method of delivering a support member around the native valve leaflets according to the disclosed embodiments.

FIGS. 2-7 illustrate an exemplary method for implanting the valve prosthesis 1 in a native mitral valve 5 of a patient. The method shown in the figures and described below is equally applicable to a prosthesis 1 for functional replacement of the native tricuspid valve. FIGS. 2 and 3 are cross-sectional 3-chamber views through the left side of a patient's heart showing the acts performed in delivering the support member 80 using an arterial retrograde approach through a patient's aortic arch to a position adjacent the aortic valve 20 in the LVOT. FIGS. 4-7 are cross-sectional 3-chamber views through the left side of a patient's heart showing the acts performed in deploying the tubular body 30 and having it engage the native valve leaflets via a trans-septal approach.

FIG. 2 shows a first delivery catheter 50 delivered into the left ventricle 10 of a patient's heart via the aorta and through the aortic valve 20. The first delivery catheter 50 can be positioned so that it is not directly centered about the outflow side of the native mitral valve 5, but rather is offset from the center. For instance, the first delivery catheter 50 can be positioned so that it is on an outer side of the space enclosed by chordae tendineae 13. The chordae tendineae 13 are attached to a distal edge 121*a*, 121*b* of each of the native mitral valve leaflets 12*a*, 12*b* and to the papillary muscles 14 of the left ventricle 10.

The first delivery catheter 50 may include a first delivery sheath and a second delivery sheath that each include inner lumens and are housed within and can be advanced through the inner lumen of the first delivery catheter 50. An elongate member 75, such as a guidewire, may be advanced from the first delivery catheter 50 around the native valve leaflets 12*a*, 12*b*. The elongate member 75 may contact and deflect from a wall defining the left ventricle 10 so as to curve around the native leaflets 12*a*, 12*b*, for example, at a position near the native valve annulus 11. Alternatively, the elongate member 75 may be pre-shaped to curve around native leaflets 12*a*, 12*b*, or the deliver catheter 50 or a delivery sheath housed therein may be pre-shaped so as to curve around the native valve lefts 12*a*, 12*b* once advanced from a distal end of the first delivery catheter 50. The elongate member 75 is guided around the native leaflets 12*a*, 12*b* and not around the chordae tendinae 13, which could otherwise undesirably result in elongate member 75 being caught on or placed between chordae tendinae 13. The elongate member 75 may form a contractible loop (e.g., like a lasso) around the native valve leaflets 12*a*, 12*b* having a greater diameter than an outer diameter of the leaflets 12*a*, 12*b*, as shown in FIG. 2.

The elongate member 75 may form the loop shown in FIG. 2 by catching or snaring a free end of the elongate member 75 and pulling the snared free end of the elongate member 75 back through the catheter 50 to thereby form the loop. The free end of the elongate member 75 may be snared or caught by a catching mechanism, such as a snare, catching wire, forceps, magnet, or any other suitable mechanism. The catching mechanism can be advanced through the delivery catheter 50 or a delivery sheath housed therein to capture the free end of the elongate outer member 75 and then can be retracted back through the delivery catheter 50 or a delivery sheath housed therein to form the loop shown in FIG. 2.

Then, as shown in FIG. 3, the support member 80 may be guided over the elongate member 75 so as to form a ring around the native valve leaflets 12*a*, 12*b*. The ends of the support member 80 may be coupled to one another to form the ring by any suitable coupling mechanism, including, but not limited to, any one or more of: magnets having opposite polarities, clips, hooks, barbs, snares, arms, tabs, lock, flap, grooves, recesses, and the like. For example, one end of the support member can be designed to be received within an inner cavity or open lumen at the other end of the support member 80 to form a ring around the leaflets. The one end of the support member may have a conical shape designed to be received within the cavity at the other end. To further secure the two ends together, the one end may also include a magnet, lock, clip, hook, barb, snare, arm, tab, flap, groove, recess, or any other engageable member for engaging an inner surface of the cavity or lumen of the other end. The inner surface of the cavity or lumen at the other end may include, for example, a magnet, lock, clip, hook, barb, snare, arm, tab, groove, recess, or any other engageable member for engaging the outer surface of the one end of the support member 80.

The technique for introducing the support member 80 around the native valve leaflets by being guided over the elongate member 75 is not limited to the exemplary embodiment illustrated in FIGS. 2 and 3. For example, in some embodiments, the elongate member 75 may be eliminated altogether, and the support member 80 may be advanced around the native valve leaflets 12*a*, 12*b* to form a ring there around without being advanced over the elongate member 75. For instance, the support member 80 may be pre-shaped to curve around the native leaflets 12*a*, 12*b* once advanced from the distal end of the delivery catheter 50, or the delivery catheter 50 or a sheath disposed therein may be pre-shaped so as to curve around the native leaflets 12*a*, 12*b*.

As shown in FIG. 4, the support member 80 can be left free floating around the native leaflets 12*a*, 12*b* in between the native valve annulus 11 and the papillary muscles 14 while a second delivery catheter 60 is delivered inside of the native valve 5 for implanting the tubular body 30 via a trans-septal approach. In particular, in FIG. 4, the second delivery catheter 60 is introduced through venous access and a puncture through the inter atrial septum. However, the second delivery catheter 60 may be introduced through any other suitable approach. Exemplary approaches for introducing the first and second delivery catheters 50, 60 are discussed below.

The second delivery catheter 60 includes the tubular body 30 in a compressed state. For example, the tubular body 30 may be disposed inside an inner lumen of the second delivery catheter, and can be radially compressed to facilitate delivery of the prosthesis 1 to the native valve. The second delivery catheter 60 is advanced through the left atrium 15 inside the native leaflets 12*a*, 12*b* (e.g., anterior and posterior leaflets) of the native mitral valve, and into the left ventricle 10. The catheter 60 can be positioned in the left ventricle 10 such that the shoulder 47 of the compressed tubular body 30 or a proximal end of the outflow end section 302 is positioned distal of the support member 80 in an axial direction. That is, the shoulder 47 the proximal end of the outflow end section 302 can be distally spaced from the support member 80 in a direction away from the native valve 5 (e.g., further into the left ventricle 10). The second delivery catheter 60 may be positioned in the left ventricle 10 such that the shoulder 47 or proximal end of the outflow end portion 302 is distal of the a distal edge 121*a*, 121*b* of at least one of the native leaflets 12*a*, 12*b* in the axial direction. For instance, the second delivery catheter 60 may be positioned in the left ventricle 10 such that the shoulder 47 or proximal end of the outflow end portion 302 is distal of the distal edge 121*a* of at least the anterior leaflet 12*a* of the mitral valve 5, and/or a distal edge 121*b* of the posterior leaflet 12*b* of the native mitral valve 5.

Likewise, when the prosthesis 1 is implanted into the native tricuspid valve, the second delivery catheter 60 may be position such that the shoulder 47 and/or proximal end of the outflow end portion 302 of the tubular body 30 is distal of the support member 80, which is disposed around the native tricuspid valve leaflets in between the native annulus and papillary muscles, and/or is distal of a distal edge of one, two, or all three of the native leaflets (e.g., the anterior, septal, and/or posterior leaflets) of the native tricuspid valve.

The "distal edge" of the leaflets as used herein may refer to an edge of the leaflets where the chordae tendinae 13 attach to the native leaflets, and/or may refer to an edge of the native valve leaflets that extends farther into a ventricular chamber of the heart (e.g., in a direction away from an atrial chamber and/or the native valve annulus) than a remaining part of the native leaflet. For instance, for the native mitral valve 5, a distal edge 121*a*, 121*b* may be an outer edge of the native valve leaflets 12*a*, 12*b* that extends deeper into the left ventricle 10 in a direction away from the left atrium 15, e.g., during diastole. For the native tricuspid valve, a distal edge may be an outer edge of the native valve leaflets that extends deeper into the right ventricle in a direction away from the right atrium, e.g., during diastole.

Once the second delivery catheter 60 has been positioned in the left ventricle 10, the tubular body 30 can be partially deployed from the second delivery catheter 60, as illustrated in FIG. 5. In particular, the tubular body 30 can be partially deployed from the second delivery catheter 60 such that the outflow end portion 302, but not an inflow end portion 301, is deployed at a position distal of the distal edge 121*a*, 121*b* of at least one of the native valve leaflets 12*a*, 12*b*. For instance, the tubular body 30 can be partially deployed starting from the outflow end 35 until the engagement mechanism, such as the shoulder 47 or the groove 45, deploys from the delivery catheter.

The tubular body 30 may be partially deployed such that the leaflet engagement mechanism (e.g., clips 46, shoulder 47, groove 45, arms 48, barbs or hooks 49) or a proximal end of the outflow end portion 302 is positioned distal of the distal edge 121*a*, 121*b* of at least one of the native leaflets 12*a*, 12*b*. For example, in FIG. 5, the outflow end portion 302 is partially deployed until the shoulder 47 and at least part of the groove 45 are deployed at a position distal of the distal edge 121*a*, 121*b* of the native leaflets 12*a*, 12*b*.

The leaflet engagement mechanism may be spaced in the distal direction from the distal edge 121*a* of at least the anterior leaflets 12*a* and/or may be spaced in the distal direction from the distal edge 121*b* of the posterior leaflet 12*b* of the native mitral or tricuspid valves (and/or the septal leaflet of the native tricuspid valve). By deploying the outflow end portion 302 of the tubular body 30 such that the leaflet engagement mechanism is distal of the distal edge 121*a*, 121*b* of the native valve leaflets 12*a*, 12*b*, the native leaflets can be at least partially captured and moved by the leaflet engagement mechanism to a position less likely to obstruct the LVOT or RVOT.

The tubular body 30 can be partially deployed from the second delivery catheter 60 by, for example, retracting a sheath of the second delivery catheter 60 until the engagement mechanism (e.g., clips 46, shoulder 47, arms 48, barbs or hooks 49) or a proximal end of the outflow end portion 302 deploys from the catheter 60. Thus, in the partially deployed state, the outflow end portion 302 radially expands to an expanded stated, as shown in FIG. 5, while the inflow end portion 301 remains in a radially compressed state inside a lumen of the second delivery catheter 60. The tubular body 39 may be radially self-expandable such that outflow end portion 302 automatically expands once it deploys from a distal end of the catheter 60, or may be balloon expandable.

Then, as shown in FIG. 6, the second delivery catheter 60 is moved in a proximal direction towards the left atrium 15 such that the partially deployed tubular body 30 is moved in the proximal direction. That is, the deployed outflow end portion 302 is moved in the proximal direction towards the left atrium 15 and the native mitral valve annulus 11. As a result, the leaflet engagement mechanism, such as the shoulder 47 or any of the other leaflet engagement mechanism disclosed herein, engages the distal edge 121*a*, 121*b* of at least one of the native leaflets 12*a*, 12*b* and then lifts the native leaflet(s) 12*a*, 12*b* in the proximal direction toward the left atrium 15. The native valve leaflet can thus be captured by the engagement mechanism in an at least partially folded up state at a position on a proximal side of the outflow end portion 302.

As shown in FIG. 6, the native valve leaflets 12*a*, 12*b* are lifted towards the support member 80, which is still free floating between the native annulus 11 and the papillary muscles 14. As such, the native valve leaflet 12*a*, 12*b* can be captured by the engagement mechanism in a folded up state in between the engagement mechanism and the support member 80. The leaflets 12*a*, 12*b* can be pinched or clamped or otherwise sandwiched in between the engagement means, such as the shoulder 47, and the support member 80. The leaflets 12*a*, 12*b* may be in a folded up, bunched up, or rolled up state in between the engagement means and the support member 80 as shown in FIG. 6. For example, the leaflets 12*a*, 12*b* may be bunched up in between the support member 80 and the engagement means, such as the shoulder 47 or any of the other engagement means disclosed herein.

As a result, the native leaflets 12*a*, 12*b* do not block or entirely block the LVOT or RVOT such that blood can flow from the ventricular chamber to the aorta or pulmonary artery. Additionally, the native leaflets 12*a*, 12*b* do not cover or entirely block the lateral openings 421 in the fabric 42 on the outflow end portion 301 of the tubular body 30. Thus, the lateral openings 421 in the fabric 42 may remain mostly or entirely free of obstruction by the leaflets 12*a*, 12*b*. This permits blood flow through the lateral openings 421 and avoids or reduces obstruction of the LVOT or RVOT.

In some embodiments, just one of the leaflets 12*a*, 12*b* may be engaged by the engagement means and lifted in the proximal direction so as to be positioned between the engagement means and the support member 80. For instances, just the anterior leaflet 12*a* may be engaged by the engagement means, e.g., shoulder 47, and lifted in the proximal direction so as to be sandwiched between the engagement means and the support member 80. As such, a lateral opening 421 in the fabric 42 on the anterior side of the outflow end portion 302 of the tubular body can be substantially or entirely uncovered by the native anterior leaflet 12*a* so as to permit blood flow therethrough to the aorta 20. Alternatively, just the posterior leaflet 12*b* may be engaged and lifted by the engagement means in the proximal direction so as to be sandwiched between the engagement means and the support member 20.

Once the leaflet(s) 12*a*, 12*b* have been captured by the engagement means and lifted in the proximal direction, the inflow end portion 301 of the tubular body 30 can be deployed from the second delivery catheter 60. FIG. 7 shows the tubular body 30 fully deployed in the native mitral valve 5 with the native leaflets 12*a*, 12*b* sandwiched between the outflow end portion 302 and the inflow end portion 301 of the tubular body 30. Alternatively, just one of the leaflets 12*a*, 12*b* (e.g., the anterior leaflet) may be captured between the outflow end portion 302 and the inflow end portion 301 when the tubular body 30 is fully deployed in the native valve 5.

After the tubular body 30 is fully deployed, the at least one native valve leaflet 12*a*, 12*b* can be captured by the engagement mechanism in a folded up state proximal of the outflow end 35 of the tubular body 30, for example on a proximal side of the outflow end portion 302. Upon implantation of the prosthesis, the leaflets can thus be immobilized in an at least partially folded up or bunched up state. The may avoid undesirable leaflet motion, such as systolic anterior motion in the LVOT. Additionally, the immobilized native leaflets 12a, 12b in the at least partially folded up or bunched up state between the inflow end portion 301 and the outflow end portion 302 can facilitate sealing around the valve. The at least one native valve leaflet 12a, 12b can be captured by the engagement mechanism at a position proximal of a lateral opening 421 in the fabric 42 such that the at least one native valve leaflet 12a, 12b does not obstruct the lateral opening 421.

When a support member 80 is used in combination with the tubular body 30, the leaflets 12a, 12b can also be sandwiched between the engagement mechanism and the support member 80. For example, in FIG. 7, the leaflets 12a, 12 are sandwiched between (i) the ring 80 and (ii) the shoulder 47 and groove 45 of the tubular body 30. Alternatively, the support member 80 may be used in combination with any engagement mechanism, or the support member 80 may be omitted. The lateral openings 421 in the fabric 42 on the outflow end portion 302 are also free of obstruction from the native valve leaflets 12a, 12b, which reduces the risk of obstruction of the LVOT (or the RVOT in the case of the tricuspid valve).

Although the exemplary method for implanting the prosthesis 1 and the support member 80 described above utilizes arterial retrograde approach through a patient's aortic arch (for delivering the support member 80) and a trans-septal approach for delivering the tubular body 30, any other suitable technique may be used. For instance, the valve prosthesis 1 and support member 80 may be implanted within the patient's heart valve by any one or more of the following approaches: (1) an arterial retrograde approach entering the heart cavity over the aorta, (2) through a venous access and through a puncture through the inter atrial septum (trans-septal approach), (3) over a puncture through the apex of the heart (trans-apical approach), (4) over a puncture through the atrial wall from outside the heart, (5) arterial access (e.g., from the femoral artery through a puncture in the groin), (6) directly through the vena cava and into the right atrium (for a tricuspid valve replacement, for example), or (7) any other approach known to a skilled person.

In the above exemplary method, the support member 80 was delivered around the native valve leaflets 12a, 12b before the tubular body 30 was delivered inside the native valve 5. Alternatively, the tubular body 30 could be delivered inside the native valve 5 in between the leaflets 12a, 12b before the support member is introduced around the native valve leaflets 12a, 12b. In such embodiments, the tubular body 30 may be first partially deployed from the delivery catheter 60 such that only the outflow end portion 302 is deployed. The outflow end portion 302 may be moved in the proximal direction (e.g., by moving the catheter 60) to engage and lift the native leaflets 12a, 12b via the engagement means. The support member 80 may be introduced either before or after the inflow end portion 301 of the tubular body 30 is deployed from the delivery catheter. After circumventing the native leaflets 12a, 12b, the diameter of the support member 80 and/or elongate member 75 may be reduced to help secure the leaflets 12a, 12b into engagement with the engagement means, such as the shoulder 47 and/or the groove 45 on the tubular body 30.

In the above exemplary method, two delivery catheters 50, 60 were used to implant the support member 80 and the tubular body 30. However, the method is not limited to this, and may involve only a single delivery catheter for both of the support member 80 and the tubular body 30, or may be include more than two delivery catheters 50, 60.

The disclosed methods of implanting valve prosthesis 1 may result in fixation of the tubular body 30 in the patient's native valve with minimal or no obstruction of the LVOT or RVOT.

The illustrated exemplary embodiments of the prosthesis and method of implantation as set forth above are intended to be illustrative and not limiting and can be combined. Various changes may be made without departing from the spirit and scope of the disclosure.

What is claimed is:

1. A method for implanting a prosthetic valve in a heart of a patient, comprising:
    advancing a delivery catheter to a position between native valve leaflets of a native mitral or tricuspid valve,
        the delivery catheter containing a radially self-expandable tubular body, the tubular body extending in an axial direction from an inflow end to an outflow end, and including a lumen in which the prosthetic valve is disposed, and a fabric attached the tubular body so as to cover a part of an outer surface of the tubular body;
    partially deploying the tubular body from the delivery catheter such that an outflow end portion of the tubular body is deployed from the delivery catheter while an inflow end portion of tubular body remains in a radially compressed state inside a lumen of the delivery catheter, the outflow end portion being deployed at a position distal of a distal edge of at least one of the native valve leaflets;
    moving the delivery catheter in a proximal direction towards an atrial chamber of the heart such that the outflow end portion of the partially deployed tubular body engages the distal edge of the at least one native valve leaflet and lifts the at least one native valve leaflet in the proximal direction towards the atrial chamber of the heart; and
    then deploying the inflow end portion of the tubular body such that the tubular body is fully deployed and the at least one native valve leaflet is captured between the outflow end portion and the inflow end portion of the tubular body.

2. The method according to claim 1, wherein the outflow end portion includes an engagement mechanism configured to engage the at least one native valve leaflet and lift the at least one native valve leaflet in the proximal direction when the delivery catheter is moved in the proximal direction toward the atrial chamber of the heart.

3. The method according to claim 2, wherein the engagement mechanism includes at least one element selected from the group consisting of:
    a groove or recess formed in the outer surface of the tubular body,
    a shoulder or bulge formed in the outer surface of the tubular body,
    an arm extending from the outer surface of the tubular body,
    a clip disposed on the outer surface of the tubular body,
    a hook disposed on the outer surface of the tubular body, and
    a barb disposed on the outer surface of the tubular body.

4. The method according to claim 2, wherein the engagement mechanism includes a groove formed in the outer surface of the tubular body, and a shoulder formed on an outflow side of the groove.

5. The method according to claim 2, wherein, after the tubular body is fully deployed, the at least one native valve leaflet is captured by the engagement mechanism in an at least partially folded up state proximal of the outflow end of the tubular body along the axial direction.

6. The method according to claim 2, wherein the fabric on the tubular body includes a lateral opening arranged such that the outflow end portion of the tubular body is at least partially uncovered by the fabric to enable blood flow therethrough.

7. The method according to claim 6, wherein, after the tubular body is fully deployed, the at least one native valve leaflet is captured by the engagement mechanism at a position proximal of the lateral opening in the fabric along the axial direction such that the at least one native valve leaflet does not obstruct the lateral opening.

8. The method according to claim 2, wherein the tubular body is partially deployed starting from the outflow end until the engagement mechanism deploys from the delivery catheter at a position distal of the distal edge of the at least one native valve leaflet.

9. The method according to claim 2, wherein the engagement mechanism is positioned at an axial height of prosthetic leaflets of the prosthetic valve, or proximal of the prosthetic leaflets along the axial direction.

10. The method according to claim 2, wherein the engagement mechanism has a roughened outer surface for increased friction.

11. The method according to claim 1, further comprising delivering a support member to form a ring around native valve leaflets of the native mitral or tricuspid valve.

12. The method according to claim 11, wherein, after the tubular body is fully deployed, the at least one native valve leaflet is captured between the support member and the tubular body in an at least partially folded up state proximal of the outflow end portion along the axial direction.

13. The method according to claim 12, wherein the native valve leaflet is pinched or clamped between the support member and the outer surface of the tubular body after the tubular body is fully deployed.

14. The method according to claim 11, wherein:
the tubular body includes a groove formed in the outer surface between the inflow end portion and the outflow end, and
the at least one native valve leaflet is captured in an at least partially folded up state in the groove between the support member and an outer surface of the groove after the tubular body is fully deployed.

15. The method according to claim 14, wherein:
the tubular body further includes a shoulder formed on an outflow side of the groove along the axial direction,
the tubular body is partially deployed starting from the outflow end until the shoulder deploys from the delivery catheter at a position distal of the distal edge of the at least one native valve leaflet, and
the shoulder engages the distal edge of the at least one native valve leaflet and lifts the at least one native valve leaflet in the proximal direction when the delivery catheter is moved in the proximal direction towards the atrial chamber of the heart.

16. The method according to claim 15, wherein the distal edge of the at least one native valve leaflet is captured between the shoulder and the support member after the tubular body is fully deployed.

17. The method according to claim 15, wherein the ring formed by the support member is larger in circumference than the groove, but smaller in circumference than the shoulder.

18. The method according to claim 15, wherein the shoulder has a largest circumference of the outflow end portion of the tubular body.

19. The method according to claim 1, wherein the at least one native valve leaflet includes an anterior mitral valve leaflet or an anterior or septal tricuspid valve leaflet, and the patient is at risk of obstruction of a left ventricular outflow tract or a right ventricular outflow tract by the anterior mitral valve leaflet or the anterior or septal tricuspid valve leaflet.

20. The method according to claim 1, wherein when the tubular body is partially deployed, an entirety of the partially deployed tubular body that is exposed from the delivery catheter is spaced from the distal edge of the at least one native valve leaflet in a distal direction extending away from the atrial chamber of the heart towards a ventricular chamber of the heart.

* * * * *